United States Patent [19]
Burnham et al.

[11] Patent Number: 5,997,812
[45] Date of Patent: *Dec. 7, 1999

[54] METHODS AND APPARATUS FOR THE APPLICATION OF COMBINED FIELDS TO DISINFECT FLUIDS

[75] Inventors: Jeffrey C. Burnham, Naples, Fla.; Robert S. Reimers, Metairie, La.; Jery E. Barton, Naples, Fla.; Warren S. Bankston, Covington, La.

[73] Assignees: Coolant Treatment Systems, L.L.C., Naples, Fla.; Administrators of The Tulane Educational Fund, New Orleans, La.

[*] Notice: This patent issued on a continued prosecution application filed under 37 CFR 1.53(d), and is subject to the twenty year patent term provisions of 35 U.S.C. 154(a)(2).

[21] Appl. No.: 08/690,982

[22] Filed: Aug. 1, 1996

Related U.S. Application Data

[63] Continuation-in-part of application No. 08/667,028, Jun. 20, 1996.

[51] Int. Cl.$^6$ ........................................ A61L 2/00
[52] U.S. Cl. .................... 422/24; 210/695; 210/748; 250/455.11; 422/1
[58] Field of Search ................. 422/24, 186.3, 422/23, 1; 210/695, 754, 748, 760, 764, 766, 407; 250/455.11

[56] References Cited

U.S. PATENT DOCUMENTS

| | | |
|---|---|---|
| 2,147,857 | 2/1939 | O'Brein . |
| 2,340,890 | 2/1944 | Lang et al. . |
| 3,060,339 | 10/1962 | Moriya . |
| 3,230,137 | 1/1966 | Ellison . |
| 3,433,946 | 3/1969 | Hardwick . |
| 3,456,107 | 7/1969 | Robertson . |
| 3,462,597 | 8/1969 | Young . |
| 3,471,693 | 10/1969 | Veloz . |
| 3,485,576 | 12/1969 | McRae et al. . |
| 3,527,940 | 9/1970 | Balanca et al. . |
| 3,550,782 | 12/1970 | Veloz . |
| 3,562,520 | 2/1971 | Hippen ................... 250/372 |
| 3,567,026 | 3/1971 | Kolm ..................... 210/222 |
| 3,608,718 | 9/1971 | Aubrey, Jr. et al. ........ 209/214 |
| 3,634,025 | 1/1972 | Landry ................... 250/436 |
| 3,635,819 | 1/1972 | Kaiser .................... 210/634 |
| 3,659,096 | 4/1972 | Kompanek ................. 422/24 |
| 3,669,274 | 6/1972 | Happ et al. ............... 210/222 |
| 3,674,421 | 7/1972 | Decupper . |
| 3,676,337 | 7/1972 | Kolm ..................... 210/695 |
| 3,683,177 | 8/1972 | Veloz .................... 250/435 |
| 3,700,406 | 10/1972 | Landry . |
| 3,767,918 | 10/1973 | Graybeal ................. 250/433 |
| 3,814,680 | 6/1974 | Wood . |
| 3,837,800 | 9/1974 | Wood .................... 422/24 |
| 3,844,943 | 10/1974 | Duval .................... 210/695 |
| 3,889,123 | 6/1975 | Bosshard ................. 387/67 |
| 3,894,236 | 7/1975 | Hazelrigg ................ 250/435 |
| 3,923,663 | 12/1975 | Reid ..................... 210/251 |
| 3,948,772 | 4/1976 | Ellner ................... 210/96.1 |
| 4,008,045 | 2/1977 | Free ..................... 250/436 |
| 4,013,063 | 3/1977 | Bucalo ................... 128/843 |
| 4,017,735 | 4/1977 | Siegel ................... 250/430 |
| 4,026,805 | 5/1977 | Fowler ................... 210/223 |
| 4,028,246 | 6/1977 | Lund ..................... 210/151 |
| 4,050,426 | 9/1977 | Sanderson ................ 123/538 |
| 4,065,386 | 12/1977 | Rigby .................... 210/695 |
| 4,079,002 | 3/1978 | Iannicelli ............... 210/695 |
| 4,082,665 | 4/1978 | Schneider et al. ......... 210/91 |
| 4,108,767 | 8/1978 | Cooper ................... 210/695 |
| 4,110,208 | 8/1978 | Neal ..................... 210/695 |
| 4,141,686 | 2/1979 | Lewis .................... 250/436 |
| 4,141,830 | 2/1979 | Last ..................... 210/748 |
| 4,146,479 | 3/1979 | Brown .................... 210/222 |
| 4,188,296 | 2/1980 | Fujita ................... 210/222 |
| 4,189,363 | 2/1980 | Beitzel .................. 204/158.2 |
| 4,210,535 | 7/1980 | Risk ..................... 210/222 |
| 4,214,962 | 7/1980 | Pincon ................... 204/157.44 |
| 4,229,389 | 10/1980 | Granger .................. 261/122.1 |
| 4,230,571 | 10/1980 | Dadd ..................... 210/760 |

(List continued on next page.)

FOREIGN PATENT DOCUMENTS

| | | |
|---|---|---|
| 0712807 | 10/1995 | European Pat. Off. ........ C02F 1/48 |
| 2450612 | 4/1980 | France . |
| 25 26 674 A1 | 6/1977 | Germany .................. C02B 1/02 |
| WO9509815 | 10/1994 | WIPO ..................... C02F 1/32 |
| WO9622944 | 1/1996 | WIPO ..................... C02F 1/463 |

OTHER PUBLICATIONS

Patent Abstracts of Japan. vol. 015, No. 080 (C–0810), Feb. 25, 1991 (TOTO LTD).
Patent Abstracts of Japan. vol. 015, No. 202 (C–0834), May 23, 1991 (SUIDO KIKO KK).
Patent Abstracts of Japan. vol. 095, No. 009, Oct. 31, 1995 (PASUKO ENG KK).

*Primary Examiner*—Krisanne Thornton
*Attorney, Agent, or Firm*—Baker & Botts LLP

[57] ABSTRACT

This invention relates to apparatus and methods for the treatment of fluids with magnetic fields and, in particular, to the disinfection of contaminated fluids by treating the fluids with a high-gauss magnet followed by ultraviolet radiation. Fluids can accumulate organic and non-organic contaminants from multiple and diverse sources. Magnetic treatment enhances the ability to separate hydrophobic contaminants from the fluid and the ability of that fluid to be disinfected. A wide variety of fluids can be treated with these methods including water to be made potable, industrial water and other fluids such as coolants and lubricants, oils, petrochemicals such as fuels, and beverages. Further, fluid can be exposed to UV radiation at a flow rate sufficient to prevent occlusion of UV-transmissible surfaces in the disinfection system by contaminants in the fluid or by removing a set amount of those contaminants. Using these methods, microorganism levels can be substantially decreased with a reduced need for biocides or other anti-bacterial or anti-fungal agents. These methods are highly effective at removing contaminants and extending the useful life of fluids such as coolants and reducing or eliminating the risks posed to workers by heavily contaminated or biocide-treated coolants.

38 Claims, 11 Drawing Sheets

U.S. PATENT DOCUMENTS

| | | | |
|---|---|---|---|
| 4,273,660 | 6/1981 | Beitzel | 210/760 |
| 4,274,970 | 6/1981 | Beitzel | 210/748 |
| 4,296,066 | 10/1981 | Schenck | 422/24 |
| 4,336,223 | 6/1982 | Hillman | 422/24 |
| 4,367,410 | 1/1983 | Wood | 250/431 |
| 4,372,852 | 2/1983 | Kovacs | 210/222 |
| 4,372,860 | 2/1983 | Kaas | 210/748 |
| 4,381,754 | 5/1983 | Heckel | 123/538 |
| 4,382,866 | 5/1983 | Johnson | 210/748 |
| 4,396,582 | 8/1983 | Kodera | 422/300 |
| 4,400,270 | 8/1983 | Hillman | 210/103 |
| 4,414,951 | 11/1983 | Saneto | 123/538 |
| 4,428,837 | 1/1984 | Kronenberg | 210/222 |
| 4,438,337 | 3/1984 | Forrat | 250/436 |
| 4,460,516 | 7/1984 | Kapitanov et al. | 261/1 |
| 4,467,206 | 8/1984 | Taylor | 250/435 |
| 4,469,076 | 9/1984 | Wolff | 123/538 |
| 4,469,835 | 9/1984 | Laurin | 524/349 |
| 4,471,225 | 9/1984 | Hillman | 250/436 |
| 4,482,809 | 11/1984 | Maarschalkerweerd | 250/436 |
| 4,495,040 | 1/1985 | Panico | 204/155 |
| 4,519,919 | 5/1985 | Whyte et al. | 210/695 |
| 4,534,282 | 8/1985 | Marinoza | 99/451 |
| 4,538,582 | 9/1985 | Wakuta | 123/538 |
| 4,563,286 | 1/1986 | Johnson et al. | 210/721 |
| 4,568,901 | 2/1986 | Adam | 335/305 |
| 4,602,162 | 7/1986 | Sperry, III et al. | 250/436 |
| 4,615,799 | 10/1986 | Mortensen | 210/177 |
| 4,655,933 | 4/1987 | Johnson et al. | 210/721 |
| 4,694,179 | 9/1987 | Lew et al. | 250/431 |
| 4,716,024 | 12/1987 | Pera | 422/186.01 |
| 4,751,392 | 6/1988 | Wiesmann | 250/429 |
| 4,752,401 | 6/1988 | Bodenstein | 210/746 |
| 4,757,205 | 7/1988 | Latel | 250/435 |
| 4,766,321 | 8/1988 | Lew et al. | 250/431 |
| 4,767,932 | 8/1988 | Ellner | 250/435 |
| 4,769,131 | 9/1988 | Noll et al. | 210/85 |
| 4,798,702 | 1/1989 | Tucker | 422/24 |
| 4,849,115 | 7/1989 | Cole et al. | 210/748 |
| 4,857,204 | 8/1989 | Joklik | 210/695 |
| 4,866,282 | 9/1989 | Miripol et al. | 250/455.11 |
| 4,872,980 | 10/1989 | Maarschalkerweerd | 210/243 |
| 4,897,246 | 1/1990 | Peterson | 422/186.3 |
| 4,904,874 | 2/1990 | Ellner | 250/436 |
| 4,909,931 | 3/1990 | Bibi | 210/85 |
| 4,952,376 | 8/1990 | Peterson | 422/186.3 |
| 4,952,812 | 8/1990 | Miripol et al. | 250/455.11 |
| 4,959,142 | 9/1990 | Dempo | 210/167 |
| 4,968,437 | 11/1990 | Noll et al. | 210/748 |
| 4,968,891 | 11/1990 | Jhawar et al. | 250/438 |
| 4,971,687 | 11/1990 | Anderson | 210/85 |
| 4,983,307 | 1/1991 | Nesathural | 210/748 |
| 5,006,244 | 4/1991 | Maarschalkerweerd | 210/243 |
| 5,019,256 | 5/1991 | Ifill et al. | 210/232 |
| 5,026,477 | 6/1991 | Yen | 210/169 |
| 5,120,450 | 6/1992 | Stanley, Jr. | 210/748 |
| 5,178,758 | 1/1993 | Hwang | 210/256 |
| 5,207,921 | 5/1993 | Vincent | 210/704 |
| 5,230,792 | 7/1993 | Sauska et al. | 210/97 |
| 5,234,606 | 8/1993 | Kazama et al. | 210/748 |
| 5,248,437 | 9/1993 | Forrest | 210/695 |
| 5,258,124 | 11/1993 | Bolton et al. | 210/748 |
| 5,266,215 | 11/1993 | Engelhard | 210/748 |
| 5,288,461 | 2/1994 | Gray | 422/24 |
| 5,322,569 | 6/1994 | Titus et al. | 134/1 |
| 5,332,388 | 7/1994 | Schuerch et al. | 422/291 |
| 5,352,359 | 10/1994 | Nagai et al. | 210/192 |
| 5,366,705 | 11/1994 | Reidy | 422/243 |
| 5,368,826 | 11/1994 | Weltz et al. | 422/243 |
| 5,376,281 | 12/1994 | Safta | 210/748 |
| 5,395,592 | 3/1995 | Bolleman et al. | 422/128 |
| 5,411,143 | 5/1995 | Greene | 210/222 |
| 5,433,738 | 7/1995 | Stinson | 604/92 |
| 5,439,595 | 8/1995 | Downey, Jr. | 210/748 |
| 5,441,647 | 8/1995 | Wascher et al. | 210/695 |
| 5,443,719 | 8/1995 | Johnson et al. | 210/101 |
| 5,460,718 | 10/1995 | Weck et al. | 210/205 |
| 5,466,367 | 11/1995 | Coate et al. | 210/96.1 |
| 5,468,378 | 11/1995 | de la Toree Barreiro | 210/192 |
| 5,480,557 | 1/1996 | Kawasaki et al. | 210/695 |
| 5,494,585 | 2/1996 | Cox | 210/748 |
| 5,503,800 | 4/1996 | Free | 422/24 |
| 5,504,335 | 4/1996 | Maarschalkerweerd | 250/435 |
| 5,505,904 | 4/1996 | Haidinger et al. | 422/24 |
| 5,527,426 | 6/1996 | Marwah et al. | 162/5 |
| 5,529,688 | 6/1996 | Kacarov et al. | 210/222 |
| 5,534,156 | 7/1996 | Sanderson | 210/695 |
| 5,540,835 | 7/1996 | Sanderson | 210/167 |
| 5,597,479 | 1/1997 | Johnson | 210/192 |
| 5,622,622 | 4/1997 | Johnson | 210/192 |
| 5,635,059 | 6/1997 | Johnson | 210/192 |

METHODS AND APPARATUS FOR THE APPLICATION OF COMBINED FIELDS TO DISINFECT FLUIDS

REFERENCE TO RELATED APPLICATIONS

This patent application is a continuation-in-part of United States patent application, Ser. No. 08/667,028, filed Jun. 20, 1996.

BACKGROUND OF THE INVENTION

1. Field of the Invention

This invention relates to apparatus and methods for the disinfection of fluids and, in particular, to exposing fluids to magnetic fields and ultraviolet radiation.

2. Description of the Background

Industrial fluids such as machine tool coolants, cooling tower water and organic lubricants traditionally possess fairly short useful lives. Microbial contaminants find their way into these fluids and proliferate. Microorganisms feed on fluid components as well as contaminants that leak into the fluid. As the microorganisms flourish, the fluid becomes even more inviting to further growth as generation after generation of microbes degrade essential components of the fluid, and add even more organic nutrients to the fluid. This process of degradation creates noxious odors in the environment.

In an attempt to deal with this problem, biocides are added to fluids in an effort to destroy microorganisms or hinder microbial growth. These chemicals are quite toxic to humans and can quickly build up to toxic levels making repeated treatments impractical. Useful life for such fluids is only slightly extended. In addition, there are considerable environmental problems associated with disposal of contaminated and biocide-treated fluids, due in large part to the presence of the additives and contaminants. At present, fluid supplies tend to require frequent replacement.

Industrial fluids were commonly discarded by dumping in drains, sewers and rivers, causing extensive and prolonged environmental impact. In 1976, the EPA ruled that fluids such as oil-based coolants were contaminated waste and must be treated or a new way of disposal found (Public Law 94-580; Oct. 21, 1976). To meet this directive, centrifugation or filtration were considered as the primary choices for selective removal of contaminants. Filtration, although useful for removing certain contaminants, fails to remove others. Further, filters often clog or break requiring more overall costs than would have been incurred by complete fluid replacement. Centrifugation, the principal means for removing contaminated oils in coolant fluids found in larger machine tool plants, has a limited treatment rate. Similarly, cyclonic separators, in which the fluid is spun, are not able to remove all of the contaminants. Design limitations prevent reduction of contaminant concentration to no less than about two percent on a practical basis. This partial removal does not prevent bacterial regrowth or breakdown of coolant and oil components. Consequently, successful filtration and centrifugation processes, while essential for recycling for useful processing operations, only prolong the life of the fluid by a few weeks.

Ultraviolet (UV) treatment has been used to disinfect clear waters and some wastewater as described in U.S. Pat. Nos. 3,634,025; 3,700,406; 3,837,800; 3,889,123; 3,894,236; 4,471,225 and 4,602,162. Each of these U.S patents describes a method touted to be designed to sterilize water-based fluids. The principal idea behind this technique was that UV radiation would penetrate the clear liquid to kill offending microorganisms. The conventional technology of UV treatment is limited because total quartz systems have a tendency to foul easily and maintenance costs were high. UV treatment proved to be unsuccessful for industrial fluids such as coolants, as coolants are opaque, or substantially so, and often contain significant levels of contaminants such as hydraulic and way oils and ferric compounds and complexes which are highly occlusive to ultraviolet light. Under these constraints, ultraviolet radiation cannot pass more than a very small distance, if at all, into the fluid stream (e.g. U.S. Pat. No. 3,456,107). These contaminants and coolants blocked UV transmission directly and also indirectly by adhering to wall surfaces of submerged quartz UV lamps or to the inner surfaces of the UV transmissible tubing in a dry system design, wherein UV lamps are kept separated from the fluid being treated.

A number of measures to prevent the degradation of industrial fluids by microorganisms have been attempted with the objective of prolonging the life of the fluid and reducing odors and health risks associated with fluid spoilage. To minimize these risks and the hazards of contaminated coolant fluids, many facilities add appreciable levels of various biocide fluids to kill and inhibit the growth of microorganisms (e.g. U.S. Pat. No. 3,230,137). In general, coolants and other fluids perform properly in the presence of these additives. However, people exposed to biocides commonly experience allergic reactions. In many cases, the biocides interacted with the skin of workers and caused various forms of hypersensitivity and dermatitis. In short, although bacterial counts can be reduced over the short term, biocides were often more problematic than the microorganisms themselves. Ultimately, the microorganisms overcome the biocides and the microbial degradation of coolant components and contaminants results in foul odors in the work environment.

Most conventional techniques, although useful in the short term, do not provide long term reduction of microbial counts in large industrial systems by more than a single log and, more importantly, only prolong coolant life for a short period despite their high cost. Other techniques such as aeration of the fluid and thorough cleaning of the lines and machines through which the coolant flows proved to be largely unsuccessful in maintaining low levels of bacterial populations. Bacteria regrow in this environment due to the presence of available nutrients, and overcome inhibitory factors introduced by aeration or chemical management. Ultimately, the bacteria take hold growing as biofilms that can produce scale deposits throughout the fluid containment and delivery system.

Other methods for the disinfection of industrial fluids include pasteurization. In this process, fluids are heated to a pasteurizing temperature for a required period of time and subsequently cooled to an operating temperature. This process is energy intensive and the costs, resulting from the heating and cooling steps, are high. Although attempts have been made to keep pasteurization temperatures below critical temperatures that destroy or denature the industrial fluids, constant temperature cycling negatively effects many of the chemicals found in the fluid. Consequently, there is a strong need for a safe and environmentally friendly method for the disinfection of industrial and other fluids.

Another problem with fluids, although not particularly coolant fluids, is the build-up of deposits in and along the walls that confine and guide the fluid along a particular path. Deposits in water-based fluids that are the most concern seem to be calcium in the form of lime, a combination of calcium oxide and calcium hydroxide, or other forms of calcium such as calcium carbonate, calcium sulfate and calcium phosphate. Scale also includes other elements such as magnesium hydroxide, zinc phosphate, sodium salts and various forms of iron oxides and silicates.

Scaling causes decreased heat transfer efficiency in, for example heat exchange systems such as radiators and cooling towers. Scaling can also seriously elevate temperatures within a scaled tube and cause over-heating of elements within a fluid system. The build-up of scale also leads to lower storage capacities in scaled tanks and reduced or complete blockage of fluid passage necessitating large costs for scale removal. These costs are often so high or the materials so damaged that complete replacement is often necessary.

Scale and other types of deposits can be corrosive to pipes and other surfaces within the fluid stream. Corrosion can be divided into at least eight unique forms, each with its own causes and effects which includes uniform corrosion, galvanic or two metal corrosion, crevice corrosion, pitting corrosion, intergranular corrosion, selective leaching, erosion corrosion and stress corrosion. The chemical constituents of the fluid on the system have a great influence on the type and extent of corrosion. An increased salt content, such as sodium, is well know to be strongly corrosive even to the most corrosion resistant materials. Scale serves as a habitat for bacteria in the fluid containment and delivery system and provides an ideal location for replication and subsequent formation of biofilms.

Attempts have been made for many years to prevent corrosion and scaling by treating the pipes themselves. In many cases, pipes would be machined to nearly absolute smoothness so that there were few places for deposits to take hold and collect. By reducing these sites it was believed that corrosion and scale formation could be significantly reduced. Alternatively, chemical compounds such as, for example, acids could be added to the fluid to prevent scaling and unwanted precipitation. However, many of these chemical compounds were damaging to the fluid or would effect subsequent use of the fluid and could not be utilized. Still other types of fluids could not be treated at all, either because the additives were harmful to the user or to the fluid itself.

Conventional methods for the control of scale formation within a system required control over solubility and nucleation and crystal growth within the fluid within the system. Acid treatment and ion exchange, two of the more common approaches, are designed to control solubility by preventing the formation of supersaturated solutions while others, including chemical inhibitors, control nucleation and crystal growth.

One of the more controversial methods for the prevention of scale and corrosion involves passing the fluid through an applied field (e.g. electrostatic, magnetic, electromagnetic). Since the 1950's, a large number of claims have been made as to why and how magnetic fields can reduce corrosion and scale formation in water-based fluids. For example, the magnetic treatment has been celebrated to reduce nucleation rates, alter the structure of crystals intimately involved with deposits, increase coagulation tendencies and reduce crystallization. Magnetic fields have also been purported to reduce precipitation rates, increase coagulation and alter the kinetics of crystal growth. Other studies have shown that magnetic water treatment produces no change to fluid conductivity, no change in material solubility and no changes in fluid pH. These reports have yet to be unscrambled scientifically. However, there do appear to be a number of real effects including reduced scaling and reduced corrosion.

The effects of magnetic treatment can be both immediate and long term. Immediate effects include reduced scaling while the magnetic field is being applied. Long-term effects, or memory, have also been observed in fluid after the magnetic field has been turned off. Scale accumulation and corrosion remain reduced for hours and sometimes days. The scientific explanation for this may be related to the rate of crystal formation. Calcium carbonate is found in at least two thermodynamic forms, the more stable calcite crystal which easily precipitates and the unstable argonite/vaterrite crystal which resists precipitation. Over time, thermodynamic considerations favor formation of calcite crystals and, thus, precipitation. Magnetic treatment favors formation of the less stable argonite/vaterrite crystals and thus, less precipitation. Once magnetic treatment has ended a period of time is required for the existing, unstable crystals to transition into the more stable calcite crystals. Thus imparting the memory effect.

Although applied fields, including magnetic treatment, have produced some level of success, microorganisms and deposits still exist as a problem in the industry.

SUMMARY OF THE INVENTION

The present invention overcomes the problems and disadvantages associated with current strategies and designs and provides new methods and apparatus for the disinfection of fluids using magnetic treatment and ultraviolet radiation.

One embodiment of the invention is directed to methods for disinfecting a contaminated fluid. These methods comprise passing the fluid through a magnetic field followed by exposure of the fluid to a disinfecting amount of ultraviolet radiation. Fluids that can be disinfected include industrial fluids such as machine tool coolants, cooling tower water, petrochemicals such as combustible fuels, and other aqueous- or organic-based fluids.

Another embodiment of the invention is directed to methods for producing potable water from most any water supply. These methods comprise exposing the water supply to a magnetic field and treating the water supply, either before or after exposure, to one or more disinfection techniques such as the addition of biocide or treatment with UV radiation. This process can be used on most any water supply including water supplies obtained from lakes and rivers, or transported over large distances or under obtained under uncertain conditions making it unsafe to drink. These methods have the further advantage of being fairly inexpensive such that large amounts of potable water can be created in a very short period of time and under nearly any working conditions.

Another embodiment of the invention is directed to methods for the removal of iron, such as ferrous and ferric complexes, from a fluid in a UV disinfection system by passing the fluid through a magnetic field. Removal of iron-containing complexes reduces the potential of the fluid for forming iron-containing deposits on the surface of UV transmissible surfaces which block significant amounts of UV radiation. Removal also improves disinfection with UV radiation, reduces the corrosive potential of the fluid and increases the economic value of the fluid itself.

Another embodiment of the invention is directed to methods for activating microorganisms in a fluid by passing the fluid through a magnetic or electrostatic field. Dormant microorganisms, such as eggs, cysts, ova and spores, germinate in response to the magnetic field. Germinated spores are much less resistant to disinfection than spores and can be easily killed. Magnetic-treated fluid can be exposed to ultraviolet radiation and/or biocides and be successfully disinfected or sterilized.

Another embodiment of the invention is directed to methods for temporarily increasing the hydrophobicity of hydrophobic components within the fluid by passing the fluid through a magnetic field. The magnetic field alters the molecular structure of chemical components of and within the fluid. Alterations include increased bond angle between carbon atoms, fragmentation of side chains and a lengthening of the molecules themselves. These changes, in part, increase the hydrophobicity of the fluid and can be maintained for a period of time sufficient to allow for subsequent manipulations such as filtration. Various components within the fluid, such as hydrophobic oils in a coolant liquid, can be efficiently removed by taking advantage of the increased hydrophobicity, fragmentation and increased length of treated molecules. Treated fluid can also be further subjected to a disinfecting amount of ultraviolet radiation or biocide.

Another embodiment of the invention is directed to fluids treated according to the methods of the invention. These fluids may be industrial fluids such as coolants and washing solutions, petrochemicals such as natural gas, gasoline or diesel fuel, or water supplies obtained from lakes or rivers. Further, fluids, such as potable water, may be disinfected to a desired level of contamination or completely sterilized. The level of microorganisms that remain after treatment can be maintained at levels acceptable to local, state or federal standards.

Another embodiment of the invention is directed to apparatus for disinfecting a contaminated fluid. The apparatus comprises a tubing system for guiding the passage of the fluid through the apparatus wherein a portion of the tubing has ultraviolet-transmissible walls. The apparatus further comprises a contaminant separation system comprising a high-gauss magnet that may be an electromagnet or a permanent magnet. The apparatus also comprises an ultraviolet radiation system for irradiating the contaminated fluid. The UV radiation system comprises a plurality of ultraviolet lamps in close proximity to the portion of ultraviolet-transmissible tubing carrying the contaminated fluid.

Another embodiment of the invention is directed to apparatus for the magnetic treatment of a fluid comprising a tubing system for guiding the fluid through the apparatus, a magnetic filter for removing ferrous and ferric complexes from the fluid, and a high-gauss magnet positioned so as to generate a magnetic field within the fluid. Magnetic treatment increases the hydrophobicity of contaminants within the fluid allowing for efficient removal.

Another embodiment of the invention is directed to apparatus for producing a supply of potable water. An apparatus comprises a tubing system, an inlet for a water supply and an outlet for potable water, a magnetic filter, a high gauss magnetic and an ultraviolet radiation treatment system. Water enters the apparatus through an inlet port and into the tubing system which guides the water through the apparatus. The magnetic filter is positioned downstream of the inlet port and removes ferrous and ferric complexes from the water supply. One or more magnets may be positioned downstream of the filter to subject the water to a high-gauss magnetic field. Another filter may be positioned downstream of the magnet to collect additional contaminants made separable by the magnetic treatment. Finally, the decontamination system treats the water with a disinfecting amount of ultraviolet radiation and makes the water suitable for human consumption. Further, the system may be electronically coupled with a diagnostic device capable of detecting infectious and potentially harmful microorganisms in the fluid. This device may be further linked with a means for controlling the addition of biocides to the fluid or for controlling passage through or intensities of the UV system. Such systems are widely useful for the production of safe and drinkable water.

Other embodiments and advantages of the invention are set forth, in part, in the description which follows and, in part, will be obvious from this description or may be learned from the practice of the invention.

DESCRIPTION OF THE INVENTION

Figure 1:
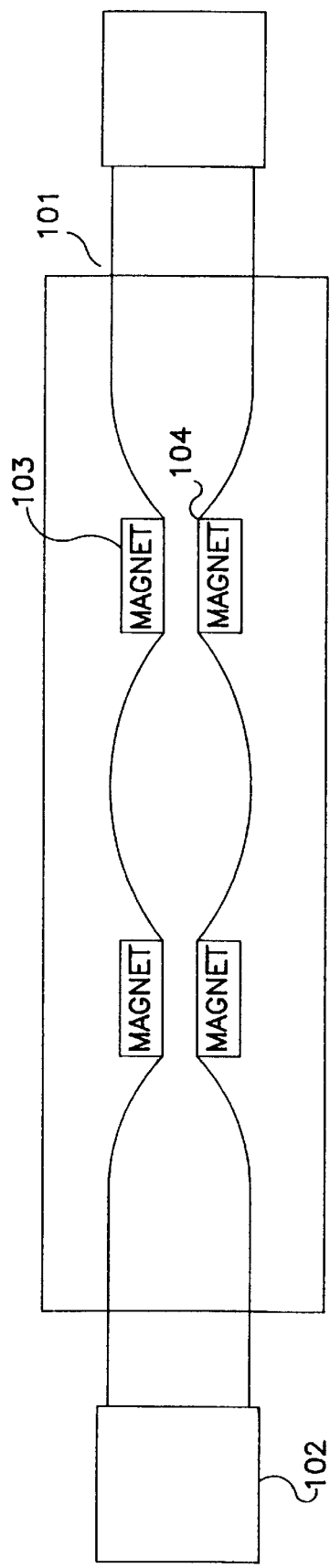
FIG. 1 Placement of magnets along a fluid flow.

As embodied and broadly described herein, the present invention is directed to novel methods and apparatus for exposing a fluid to applied fields and to fluids treated according to these methods.

Fluids used in industrial and other settings are typically either aqueous or organic. Organic fluids include, for example, processing and washing fluids, purified or semi-purified chemicals such as alcohols and acids, paints, fertilizers, lubricants and other oils, fuels such as diesel, gasoline and other hydrocarbon-containing fluids, and all forms of petrochemicals. Aqueous fluids include machine tool coolants, process-washing fluids, cooling tower water, juices and other drinks for bottling, and water supplies prepared for discharge or to be made potable. In all of these fluids, contamination due to microbial growth and leakage from other systems is a critical and constant problem.

In an industrial setting, for example, metal particles and way oils heavily contaminate coolants in assembly and manufacturing lines. In a packing plant, fruit juices, soft drinks, beers including lower alcohol beers, and other beverages become contaminated with microorganisms such as bacteria and yeast or other types of fungi. Other contaminants enter these fluids as they proceed through various mixing and bottling systems. These and other contaminants serve as an abundant nutrient base in which microorganisms flourish.

Conventional methods for the disinfection of fluids include methods for the removal and/or selective destruction of microorganisms. In filtration, microbial contaminants are removed using, for example, selectively permeable membranes. These membranes are placed in the fluid flow and selectively absorb or filter contaminants of a particular size or molecular weight. Although useful, these methods cannot be applied to all fluids and, often, it is not possible to selectively remove the contaminants without removing a significant portion of the fluid itself. Further, filtration systems are impractical for the disinfection of many types of industrial fluids. For example, certain fluids contain components essential to their function that would be filtered out along with any unwanted contaminants. Others, such as fluids with high viscosities, require multiple filtration steps and multiple filter changes making the filtration process impractical.

Another conventional method for the disinfection of fluids is to add toxic chemicals, antibiotics or other biocidal substances to kill and/or inhibit proliferating microorganisms. These methods, although useful in the short term, provide few long term benefits and pose serious problems of their own. The use of toxins, antibiotics or other chemicals to inhibit microbial growth in a fluid presents health risks to workers, as well as to the environment, and can impair the function or utility of the fluid. Other methods such as exposure to ultraviolet (UV) radiation, useful for UV transparent fluids, have proven to be ineffective for non-UV transparent (opaque) fluids. Further, these methods typically require passage of the entire volume of fluid through a thin-film. Such complications make the process prohibitively costly and sometimes impossible to perform on a large volume of fluid. Newer methods to control microbial growth include pasteurization which, effective in many settings, can damage the molecular structure of the fluid and tends to require large amounts of energy in constant temperature cycling. Further, many of the components in a fluid such as, for example, a machine tool coolant, would be altered during repeated pasteurization steps and thereby have a reduced efficacy.

It has been discovered that contaminated fluid can be disinfected by the magnetic treatment of the fluid coupled with exposing the fluid to disinfecting amounts of ultraviolet radiation. Magnetic treatment alters the molecular structure of contaminants within the fluid allowing for their efficient separation and removal. In this manner, microbial contamination of fluids, including UV-opaque fluids such as industrial fluids as well as UV-transparent fluids such as water and other water-based fluids, can be substantially reduced or eliminated. Substantially reduced means that microbial contamination is reduced such that useful life of the fluid is extended, the fluid is sufficiently disinfected to be usable for a desired property or the need for other microbial control methods such as, for example, biocides or pasteurization, is lowered.

It has also been discovered that maximum UV radiation transmission to a fluid flow can be maintained by establishing a flow rate sufficient to prevent occlusion based on the level of contaminants in the fluid, or by removing a minimum percentage of contaminants from a set flow rate to maintain maximum transmission of UV radiation. Using various combinations of these techniques, almost any fluid can be disinfected and at a cost which is substantially reduced as compared to conventional techniques.

One embodiment of the invention is directed to a method for the disinfection of a fluid by passing the fluid through a magnetic field and subjecting that fluid to a disinfecting amount of ultraviolet radiation. Magnetic treatment of fluid has multiple advantages both immediate and long term. First, in response to magnetic treatment, hydrophobic substances within a fluid become more hydrophobic and, therefore, less soluble in a hydrophilic environment. Long chain molecules such as, for example, chains of greater than about 4 carbon or silicon atoms, become extended in response to a magnetic flux or field, altering bond angles between atoms and thereby lengthening the molecule's longitudinal dimension. This effect, termed the Delong effect, makes these molecules less water soluble. In addition, the fluid becomes more polar, increasing overall electronegativity as it passes through the magnetic field as water molecules line up in response to the magnetic field. As a consequence, hydrophobic contaminants can be more easily and more effectively separated from the fluid using, for example, conventional systems based on hydrophobic/hydrophilic separation.

Further, magnetic treated flowing fluid increases in electronegativity as it passes through the magnetic field. This effect, termed the Lorentz force, is a function of magnetic field strength verses fluid velocity. The greater the field strength or the velocity of the fluid flow, the greater the electronegativity of the fluid. Hydrophobic substances and, in particular organic substances, become less soluble due to this increased eletronegativity.

Further still, magnetic treatment can impart a magnetic charge to contaminants within the fluid. Such contaminants can be segregated from the fluid and removed. Contaminants that become charged include magnetic particles such as iron that had been demagnetized by high temperatures such as encountered in many industrial processes. These particles, although previously magnetic, can loose their magnetism after heating. High temperatures reorient magnetic domains within particles. By exposing demagnetized particles to a magnetic field, magnetic domains re-establish and the particles again become magnetic. As such, the newly magnetic particles self-aggregate and can be collected using conventional magnetic or other filtration devices that are well-known to those of ordinary skill in the art.

All or any combination of these factors can be utilized to encourage the separation of hydrophobic and other contaminants from a fluid. Magnetic effects can last between less than one second to as long as about four seconds, more than a sufficient period to conduct a separation step such as, for example, filtration. However, there are also long term effects of magnetic treatment. For example, magnetic treatment fractures and/or denatures side chains of long chain molecules. These molecular fragments can be easily separated from the fluid. Contaminant molecules so modified are also less likely to cause filming and occlusion over UV transmissible surfaces.

Magnetic treatment can also be used to activate dormant microorganisms in a fluid. Although UV treatment will kill active or vegetative microorganisms in a fluid, spores, cysts and other inactive microorganisms are very resistant to conventional microbial-control technologies and will remain viable in the fluid and over time will proliferate. Passage of the fluid through a magnetic field causes spores to germinate and cells to transition out of a resting stage. These activated microorganisms are significantly more susceptible to ultraviolet radiation and can be killed. Killing of activated cells occurs with a reduced level of radiation exposure requiring reduced energy and expense as compared to that necessary without treatment. This is in direct contrast to prior methods that, using magnetic treatment attempted to kill such microorganisms as described in U.S. Pat. Nos. 5,248,437 and 4,065,386.

Activation, which includes germination, is the process of converting a dormant cell into a vegetative cell. Activation, as known to those of ordinary skill, can be spontaneous, but can also be induced by a traumatic event (e.g. pH change, heat, sulfhydryl compound) or a germinating agent (e.g. alanine, dipicolinate, $Mn^{+2}$). Passage through a magnetic field can substitute for that event or agent and thereby induce activation. Dormant microorganisms include, for example, spores, eggs, ova, cysts and other dormant cells. Magnet treatment for inducing activation of dormant cells in a fluid involves subjecting the fluid to a magnetic field of between about 2,000 to about 8,000 gauss, preferably between about 3,000 to about 7,000 gauss, and more preferably between about 4,000 to about 6,000 gauss.

In another embodiment, activation of dormant microorganisms in a fluid can be induced by imparting an electrostatic field or electric current to the fluid. The electric field or current required for activation, which may be either alternating or direct, can be generated by contacting positive and negative electrodes to the fluid. Electrodes may be placed upstream-positive and downstream-negative or upstream-negative and downstream-positive. Field strengths required for this process are generally greater than about 2,000 gauss, preferably greater than about 3,000 gauss, and more preferably greater than about 4,000 gauss.

Magnetic treatment, as known to those of ordinary skill in the art, also reduces scaling and corrosion of all surfaces exposed to the fluid (J. D. Donaldson, Tube International, *Scale Prevention and Descaling*, pp. 39–49, January 1988). These effects include changes in particle size, crystallinity, crystal phase and morphology, rate of nucleation and solubility. For example, increased magnetic strength was found to increase particle size of calcium sulphate (S. M. Grimes, Tube International, *Magnetic Effect on Crystals*, pp. 111–118, March 1988). These particles also showed increased aggregation with increases in magnetic treatment. Studies with zinc phosphate showed that particle size also decreased in response to an increasing magnetic field. In addition to changes in crystallinity, magnetic treatment can alter the morphology of crystals on various planes. Factors that can influence these events include the nature of the fluid, the magnitude of the applied current, the pH of the fluid, the fluid flow rate, the fluid conductivity, the presence or absence of impurities and other chemicals such as, for example, iron and the rare earth metals, and the concentration of the various components within the fluid. These advantages and others are described in U.S. Pat. Nos. 4,716,024; 4,568,901; 4,538,582; 4,519,919; 4,469,076; 4,460,516; 4,428,837; 4,414,951; 4,381,754; 4,372,852; 4,026,805 and 3,060,339.

Methods and apparatus for the removal of iron, such as ferrous and ferric complexes, in a UV or other disinfection system are preferred embodiments of the invention. Removal of iron-containing complexes by passing the fluid through a magnetic field reduces the potential of the fluid for forming iron-containing deposits on the surface of UV transmissible surfaces which block significant amounts of UV radiation. Removal also improves disinfection with UV radiation, reduces the corrosive potential of the fluid and increases the value of the fluid itself.

For the magnetic treatment of water and other aqueous fluids, a magnet is placed in close proximity to the fluid so as to generate a magnetic field within the fluid. The magnet may be mounted externally to the fluid path or internally, within the fluid flow. For example, one or more magnets may be positioned on an external portion of a tube with the field strengths directed into the path of the fluid within the tube. Alternatively, one or more magnets may be placed within the tube and within the fluid path. In either situation, as the fluid flows through the tube, it must pass through the magnetic field. Shown in FIG. 1 is one embodiment wherein a plurality of magnets are placed externally to the fluid. Tubing portion 101 is coupled to the tubing system through NTP coupler 102. Magnets 103 are placed at intervals along that tubing at constrictions 104 that increase fluid flow velocity through the tube portion, maximizing the Lorentz force. Magnet placement may be designed to correlate with the extent of the field strength for each magnet so as to provide optimal exposure of the fluid to the magnetic field. In those embodiments where magnets are submerged within the fluid, it may be desirable to coat the magnets with a material to prevent damage to the magnet without interfering with either transmission of the magnetic field into the fluid or causing undesirable chemical reactions with the fluid components. Such materials include, for example, synthetic polymers such as plastics and other non-conductive and relatively non-reactive materials.

The magnetic field strength of the magnet should generally be at least about 500 gauss. Depending on the fluid and the amount and type of contaminants and other substances within that fluid, field strength may vary from about 1,000 gauss to about 2,500 gauss, from about 2,000 gauss to about 5,000 gauss, from about 4,000 gauss to about 6,000 gauss, from about 6,000 gauss to about 8,000 gauss, or from about 7,000 gauss to about 9,000 gauss, or up to 10,000 gauss or more. The range of strengths useful for most applications is within about 600 to about 9,000 gauss. The magnetic field may be generated from an electromagnet or permanent magnet, as desired. One advantage to electromagnets is that field strength can be varied during operation. This can have significant advantages when a single apparatus is used to disinfect a variety of different fluids requiring different field strengths for optimal operation.

Figure 2:
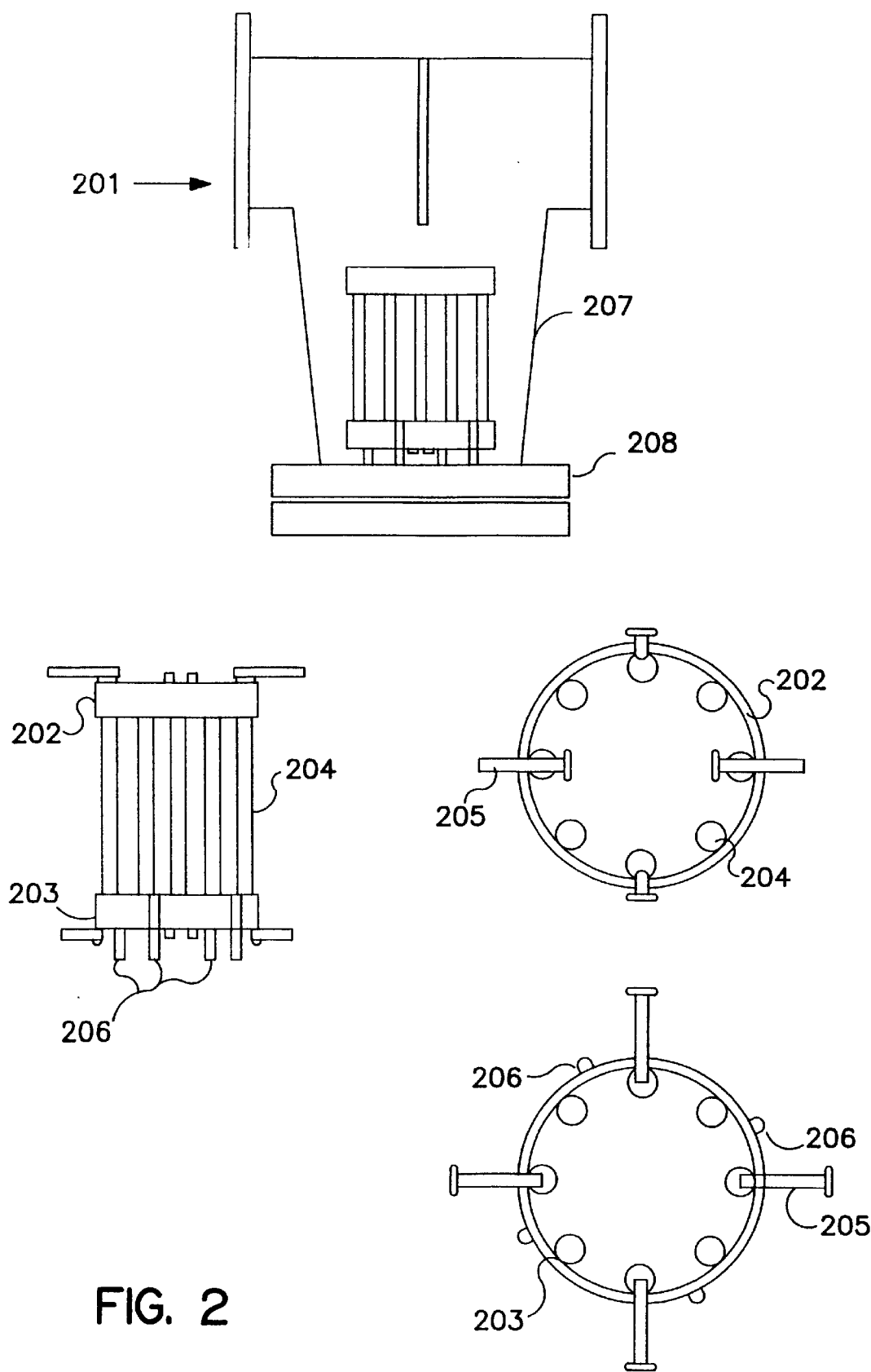
FIG. 2 Magnet schematic.

One example of such a magnet is depicted in FIG. 2 in which magnet unit 201 is shown in transparent cross-section. In the side view, top ring 202 is connected to bottom ring 203 by a series of transverse mounted magnets 204. Long bolts 205 secure top ring 202 to housing 207, and a plurality of legs 206 are attached to bottom ring 203. The magnet unit, housed in housing 207, can be fitted to connect with a portion of the tubing system containing the fluid through connector 208 which is specifically designed and composed so as to allow for an unobstructed transmission of the magnetic field into the fluid.

Figure 3:
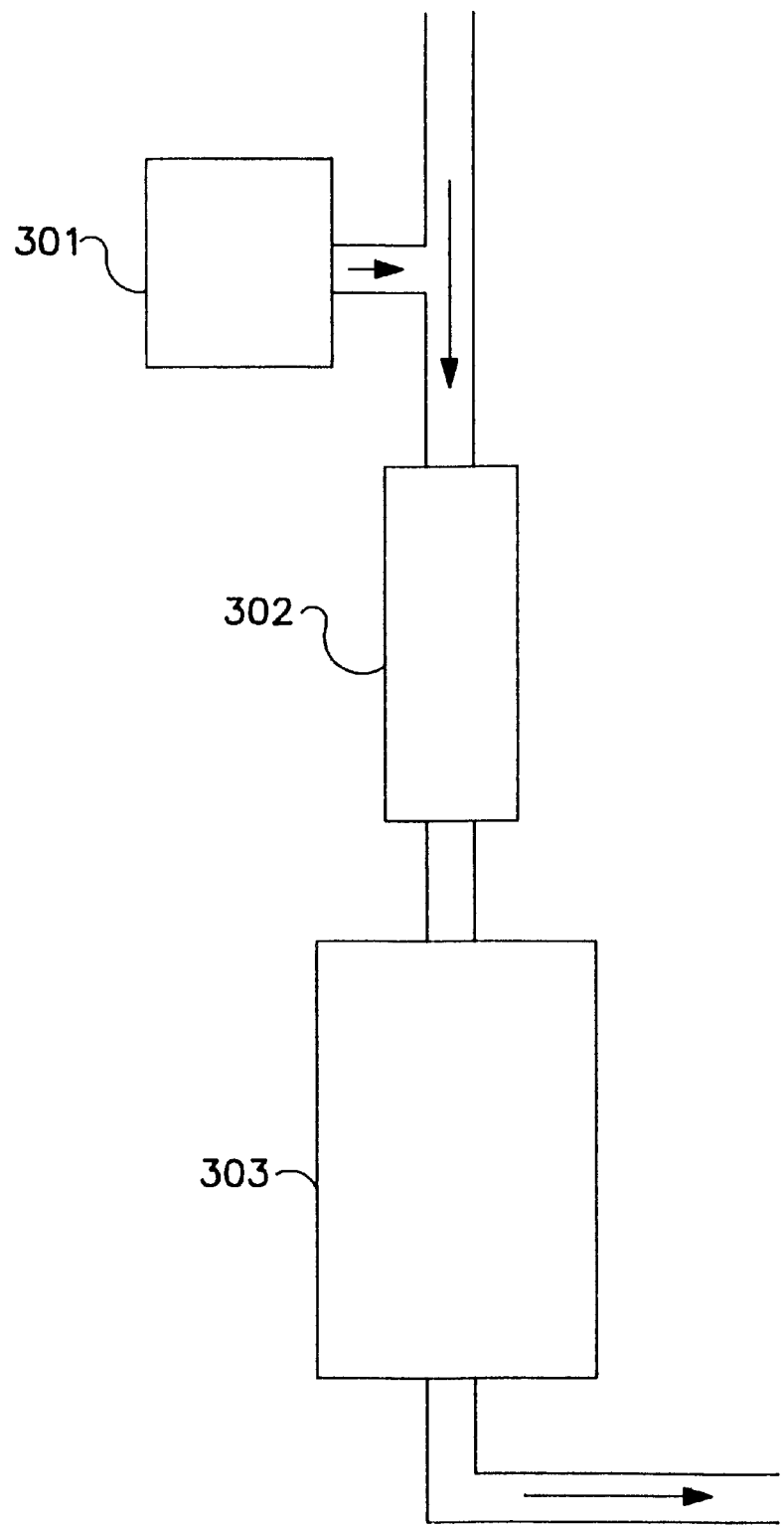
FIG. 3 Oxidant/magnetic/UV system.

Disinfection by the system can be enhanced by adding oxygenating agents and/or oxygen radicals to the fluid. As known to those of ordinary skill in the art, oxygen radicals can kill cells and other microorganisms by oxidizing surface components and essential or key biomolecules of the microbe. A typical system is depicted in FIG. 3 wherein one or more oxygenating agents such as ozone, hydrogen peroxide, iron oxides or iron hydroxides (e.g. ferrates) are added to the apparatus at section 301. Oxygenated fluid travels downstream past magnet 302 to UV disinfection system 303, disinfecting the fluid along the way. The system can also be designed to supplement the fluid with ferrous or ferric oxide, air or oxygen (gas or liquid) at section 301. By exposing the oxygen to UV radiation either from a UV system placed at section 301 or simply by allowing the downstream UV system 303 to form oxygen radicals, microorganism killing can be enhanced.

Another advantage of magnet-treated fluid is that iron complexes as well as molecular iron that may be present within the fluid will form iron oxides and hydroxides in the presence of sufficient oxygen. These iron complexes can be used to disinfect or at least to assist in the disinfection of the fluid. One of the principal oxidized forms of iron that is also a potent disinfectant are ferrates. Ferrates are highly oxygenated forms of iron, such as $Fe(OH)_x$, wherein x is from 4 to 9 and preferably 5, 6, 7 or 8, that are potent oxidizing agents. Ferrate formation can be encouraged by providing an oxygen supply to iron-containing or iron-supplemented fluid such as oxygen gas, hydrogen peroxide or ozone. Supplemental iron can be, for example, in the form of $Fe(OH)_3$.

Other methods to oxygenate the fluid include adding air or oxygen gas and exposing the fluid to ultraviolet radiation. UV radiation imparts energy to the oxygen molecules that encourage formation of oxygen radicals. Once formed, these oxygen radicals can disinfect or at least enhance disinfection of the fluid.

Flow rate of the fluid through the magnetic field is dependant on the conductivity of the fluid. In large part, fluid flow rates are related to fluid conductivities. In general, the flow velocity for organics would be about 10 times higher than for water-based fluids due to the lower conductivity of organic fluids. Aqueous fluids tend to have a higher conductivity and can be treated at about 2 meters/second and fluid velocity through the field for most water-based systems is expected to be from about 1 meter/second to about 5 meters/second, but may be more or less, as desired (e.g. from about 2 to about 5 feet per second or from about 10 to about 40 feet per second). In fluids containing increased amounts of dissolved solids, flow velocity through the magnetic field may be decreased such as, for example, to about 4 meters/second, about 3 meters/second, about 2 meters/second or less than about 1 meter/second. In fluids containing reduced amounts of dissolved solids, flow velocity may be increased. Petroleum products such as natural gas, gasoline and fuel oil have a lower conductivity and require higher flow rates of from about 5 meters/second to about 12 meters/second, and preferably from about 10 meters/second to about 15 meters/second, but can include flow speeds of from about 14 meters/second to about 20 meters/second or higher.

Fluid flow paths can be modified to maximize exposure to the magnetic field. Constrictions can be placed along the tubing to place one or more magnetic fields within the fluid path which have the added advantage of increasing or decreasing the velocity of the fluid through the magnetic field (e.g. FIG. 1). Temperatures at which the fluid is treated will generally be between about 60° F. to about 90° F., but can be lower or higher as desired. Lower temperatures may be required or useful for handling combustible or otherwise flammable fluids whereas higher temperatures may be more useful for treating large volumes of non-hazardous liquids and other fluids. Further, fluid pressures can also vary from ambient to high pressure systems with limits defined by the design of the apparatus treating the fluid.

In addition to magnetic treatment, fluid can also be subjected to ultrasound over a wide range of frequencies. Low frequency ultrasound of about 2 to about 40 watts or about 50 Hz to about 100 KHz can be used to supplement magnetic treatment by placing a sonicator either upstream or downstream of the magnet. Sonication enhances mixing and the killing effect of UV radiation.

All of these processes can be further enhanced by establishing a fluid flow rate sufficient to prevent fouling of UV transmissible surfaces while maximizing transmission of ultraviolet radiation to the fluid. Transmission can be substantially reduced by occlusion, caused by the contaminants within the fluid, of surfaces between the fluid and the radiation source. Substantially means that UV transmission is reduced to a point rendering further treatments economically or practically unfeasible. Such occlusion can be prevented by establishing a fluid flow rate that prevents occlusion. That rate is dependent on the amount of contaminants with the fluid. Consequently, in any fluid flow, a flow velocity (FV) can be set to prevent occlusion of contaminants over UV-transmissive surfaces within the system. When flow velocity is fixed, above a set critical level of contaminants, a minimum percentage of contaminants (MPC) can be removed from the fluid to achieve the set or desired FV. MPC is a variable which is dependant on the velocity of the fluid as it proceeds through the radiation treatment. The more rapid the rate of fluid flow, the less the amount of contaminants that need to be removed. The lower the flow rate, the greater the amount of contaminants that must be removed. As flow rate can be controlled, the MPC can be determined for most any fluid.

Although solid particles may be present in the fluid, MPC is a volume percentage, not a weight percentage and particle removal is not considered in the calculation. Consequently, MPC is a calculation of the volume of contaminants that must be removed from the fluid for successful disinfection by ultraviolet radiation in a flowing system. Nevertheless, with many types of fluids, particle removal may be required as there can be a synergistic effect of certain metallic particles with heavy oils that rapidly leads to occlusion of most any surface. In such cases only when both heavy oils and metallic particles are removed can occlusion be prevented and radiation treatments or other disinfection measures be successfully administered.

Fluids that can be disinfected according to the invention include, for example, liquids such as water supplies used in the preparation of potable water, carbonated beverages and other fluids under pressure, flavored drinks, fruit juices, soft drinks, beers, wines and other such liquids. In all of these examples, water supplies are necessary for creation of the product and that water as well as the resulting product passes through a maze of machinery for manufacture and bottling of the particular drink. Throughout the process, microbial contamination is a constant problem as well as problems associated with the machinery. By using a combination of contaminant removal, magnetic treatment and exposure to ultraviolet radiation, microbial contamination can be reduced to manageable levels and, if desired, completely eliminated.

Additional fluids that can be treated include petroleum products and petrochemicals such as, for example, petrolatum, natural gas, gasoline including diesel fuel, kerosene and all forms of fuel for internal combustion engines, ethylene, ammonia, synthetic petrochemicals, fertilizers, paraffin, naphthene, alcohols such as methanol, ethanol and butanol, acids, and other like chemical compounds.

Other fluids that can be treated according to the method of the invention are the industrial fluids. Industrial fluids include fluids typically used in assembly lines and other manufacturing configurations, to cool, clean and lubricate as appropriate to the specific operation being performed. Typical industrial fluids accumulate about 1% to 7% hydrophobic hydrocarbon contaminants, with the remainder of contaminants being silicon oils and soluble lubricants, all usually in an aqueous medium (e.g. water). However, non-aqueous fluids, such as electrodischarge machine fluid (EDM), can also be successfully disinfected by the practice of this invention. Preferably, fluids to be disinfected are substantially opaque. Substantially opaque fluids are fluids that do not allow lethal ultraviolet radiation energy to pass more than about 1.5 mm into the fluid.

Figure 4:
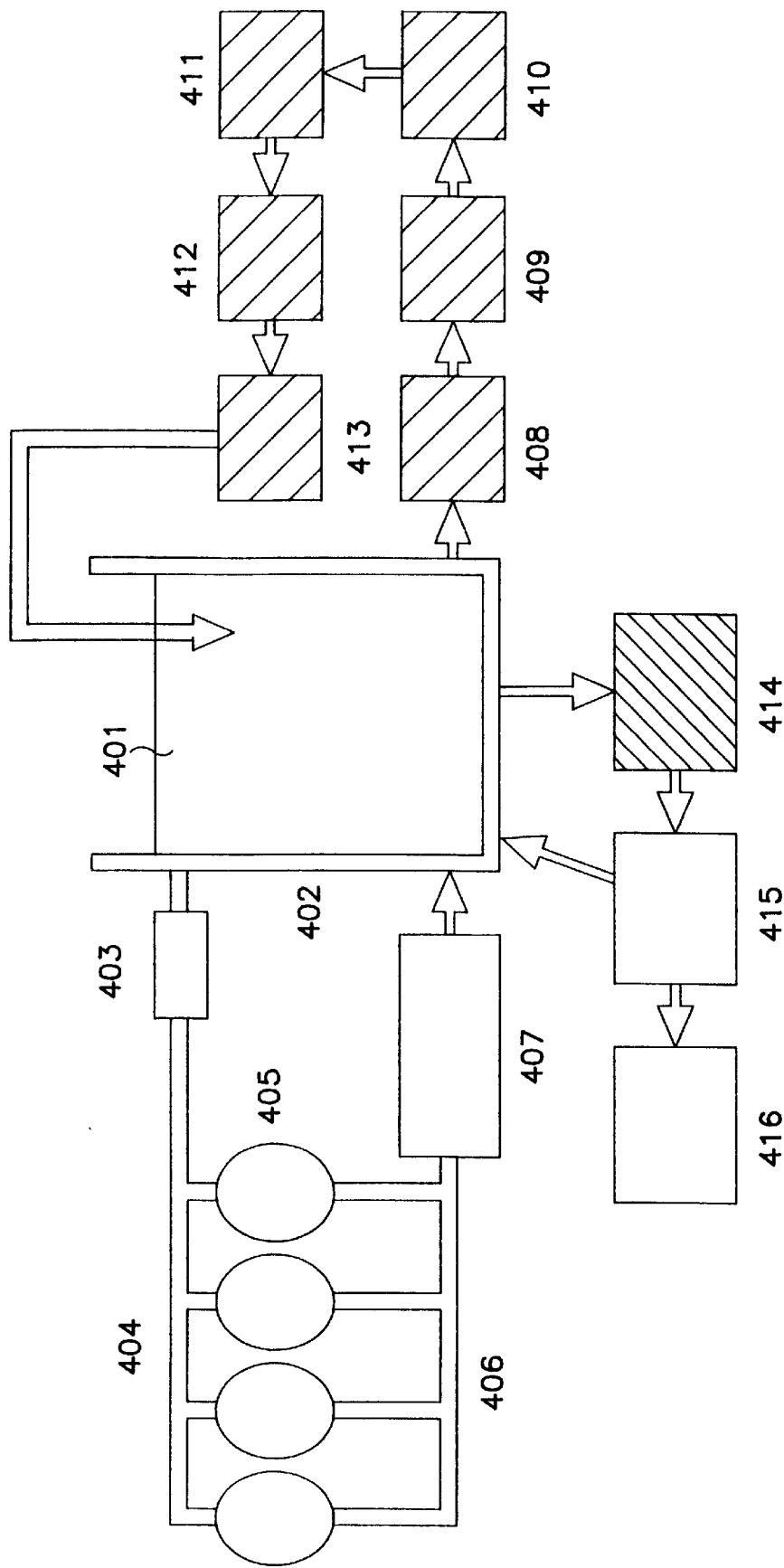
FIG. 4 Schematic of coolant fluid disinfection unit.

In large factories, manufacturing lines can be quite long and contain huge volumes of fluid such as in the manufacture of machinery, automobiles, aircraft and related parts. These lines comprise one or a plurality of machines in series (i.e. a working line), a fluid reservoir or tank, a plumbing system interconnecting the various machines and often a fluid sump with a pumping mechanism. The sizes of the tubes that guide the flow of the fluids in such system vary tremendously depending on the location in the system ranging from small to large. A typical coolant disinfection line is depicted in FIG. 4. As shown, coolant 401, starting from reservoir 402 which may be as large as 15,000 gallons or more, travels in the direction of the arrows passing through fluid pump 403, and to delivery system 404 which supplies metal working machines 405. Returning from manufacturing line through return system 406, coolant travels to iron filter screen 407 where residual iron and debris are removed, and re-enters reservoir 402. Attached to reservoir 402 is second fluid pump 408 which pumps fluid from reservoir 402 to an optional cyclonic separator 409 for further contaminant oil removal and to iron magnetic screener 410 which removes soluble ferrous and ferric complexes such as ferric hydroxides. From iron magnetic screener 410, coolant 401 flows through magnetic separator 411 where a high-strength magnetic field is applied. This magnetic field reduces the solubility of organics within coolant 401 by increasing fluid electronegativity, increasing bond angles of long chain carbons and silicons and fracturing side chains of branched hydrocarbons and hydrosilicons. Oil separation is facilitated with long-term benefits that include reduced oil filming and fouling, reduced organic and inorganic scale formation and reduced corrosion on all surfaces of the tubing system. From iron magnetic separator 411, coolant 401 travels to filter system 412 and to UV disinfection system 413, which may include a turbulence generator, and back to reservoir 402. Optionally, first fluid pump 403 and/or second fluid pump 408 may be high-velocity pumps to pass coolant 401 through magnetic system 416 and UV disinfection system 413 at a velocity sufficient to prevent UV lamp occlusion and to promote scale reduction throughout the system. From reservoir 402, coolant 401 may also enter third fluid pump 414 to be pumped through centrifuge 415 where a percentage of contaminating oil is removed before returning to reservoir 402. As the invention is not limited by the ability of UV radiation to penetrate a fluid, most all fluids used in industrial systems can be treated according to the methods of the invention.

Figure 5:
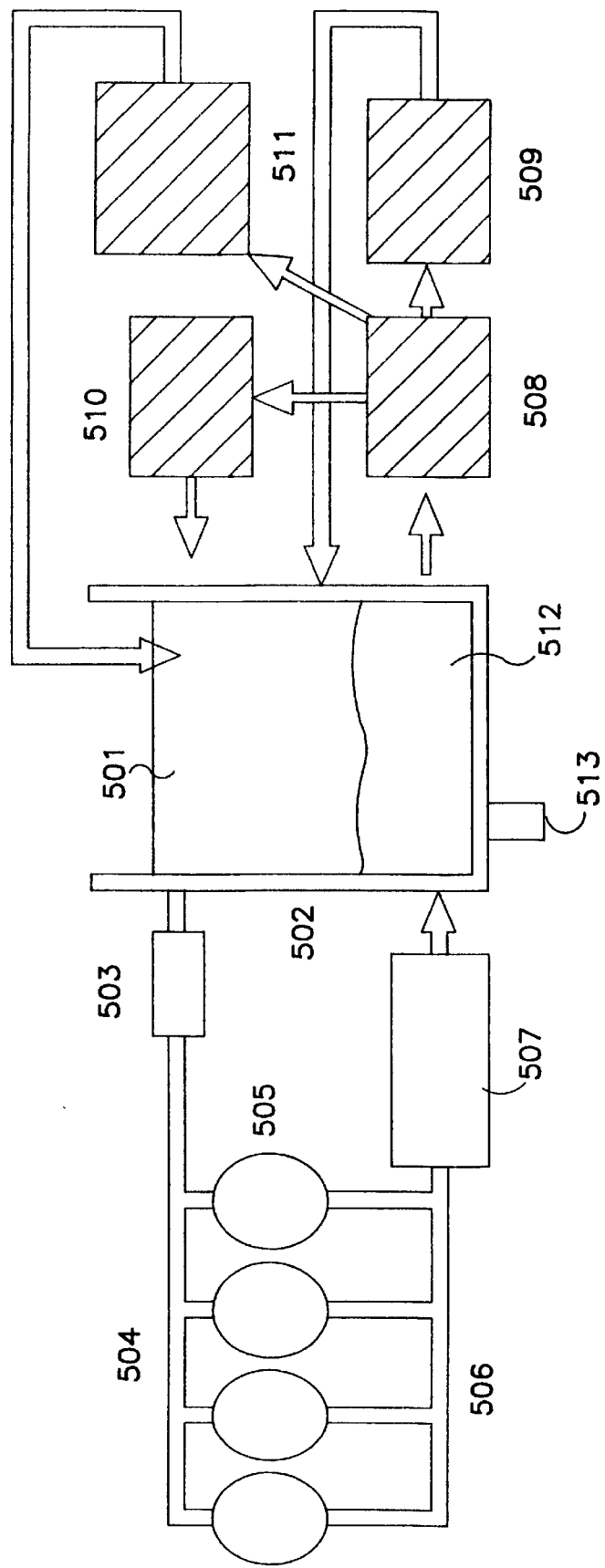
FIG. 5 Iron separation and scale reduction scheme.

A similar scheme, specifically designed to remove iron and reduce scale formation is depicted in FIG. 5. As shown, the various functions can be performed from the reservoir because it is an advantage of the invention that the manufacturing line need not be interrupted when servicing or maintaining the disinfection/separation apparatus. In this embodiment, coolant 501 flows from reservoir 502 to pump 503 whereby the coolant is pumped through delivery system 504, cutting tool machines 505, and return line 506, and through debris screen 507 to re-enter reservoir 502. Also attached to reservoir 502, but not to assembly line 504 is pump 508 and centrifuge 509, magnet/iron filter 510, and UV disinfection system 511. Each of these devices can be operated separately and independently. However, as each system operates independently, it is anticipated that sludge 512 (e.g. $CaCO_3$ and $Fe(OH)_3$) will accumulate in the reservoir. This material can be easily discharged through discharge port 513 as it will collect at the bottom of the tank. Should contaminants collect at the surface, it would be a simple matter to include another discharge port from reservoir 502 at the fluid surface. In this scheme, the process can be operated continuously.

Specific types of fluids typically found within these manufacturing lines include metal-working fluids, machine-tool coolants, machine-tool lubricants, electro-discharge machine fluid, Zyglo, electro-coating fluid, chassis-washing fluid, process-washing fluids, top-coating fluids, sonic-bath fluids, spot- and steam-welding coolants, electron-beam and laser-welding coolants, test-cell waters for metal processing, plastic molding and forming coolants, quenching fluids, recycled and recirculation fluids, and combinations thereof.

In the disinfection of industrial fluids, one or more pre-filters or particle filters are typically used to remove heavy particles such as metallic or plastic chips and filings. With industrial coolants, this step removes metallic particles which, in combination with way oils, lead to sludge formation and subsequent occlusion of UV transmissible tubing or UV lamps in the system. Prefilters are preferably comprised of metal or plastic strainers that remove the larger and coarser particles present in the fluid (e.g. metallic or plastic particles, chips and shavings). Additional filters that can be used include composite fiber-mesh filters and the like. Mesh filters contain fibers of, for example, polyester, polypropylene, nylon, Teflon, Nomex, Viscose or combinations of these materials. These fibers have a wide variety of pore sizes (e.g. 1, 2, 5, 10, 15, 20, 25, 30, 35, 40, 45, 50, 75, 100, 125, 150, 175, 200, 300, 400, 500 micron) and are commercially available. Additionally, filters may contain biological fibers comprised of, for example, peat and/or kenaf.

Once larger particles have been removed, fluid flows to a second stage filter such as, for example, a coalescent filter to remove additional contaminants. Bag filters contain fibers, structured with various pore sizes, that are adherent to the contaminant. When placed in a fluid flow, bag filters capture those contaminants that cannot pass through the pores and contaminants that adhere to the fibers. Coalescent filters, a specific type of bag filter, are commercially available that are adherent to the heavy way and hydraulic oils, such as tramp oils, common in industrial fluids. For industrial fluids, the combination of a particle filter and a separator, such as an oil separator, removes sufficient amounts of contaminant particles and oils present in the fluid to allow for successful disinfection with ultraviolet radiation. An important advantage of this combination is that both live and dead bacteria are removed from the fluid which thereby reduces the requirement for the ultraviolet system to conduct all of the killing. As dead bacteria are an important nutrient source for bacterial growth, removal of dead microbes is an important and previously unrecognized advantage. Additionally, smaller pore size filters, besides removing bacteria, can remove parasites, eggs and cysts such as, for example, Giardia, Cryptosporidium, Pseudomonads and Escherichia. Thus, smaller pore filters can facilitate the production of potable water.

Figure 6A:
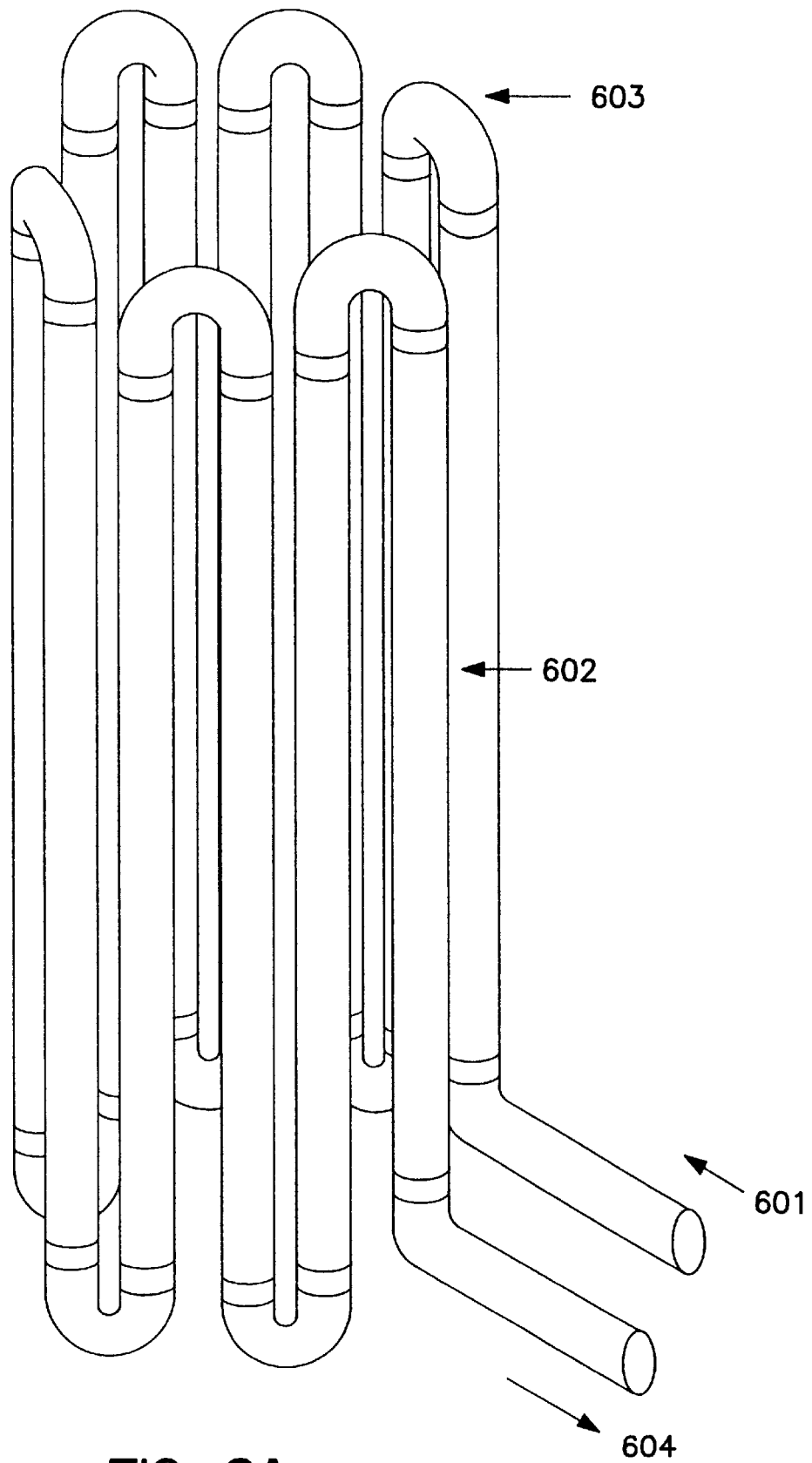
FIG. 6 Rigid tubing for model unit shown in (A) longitudinal and (B) cross-section.
Figure 6B:
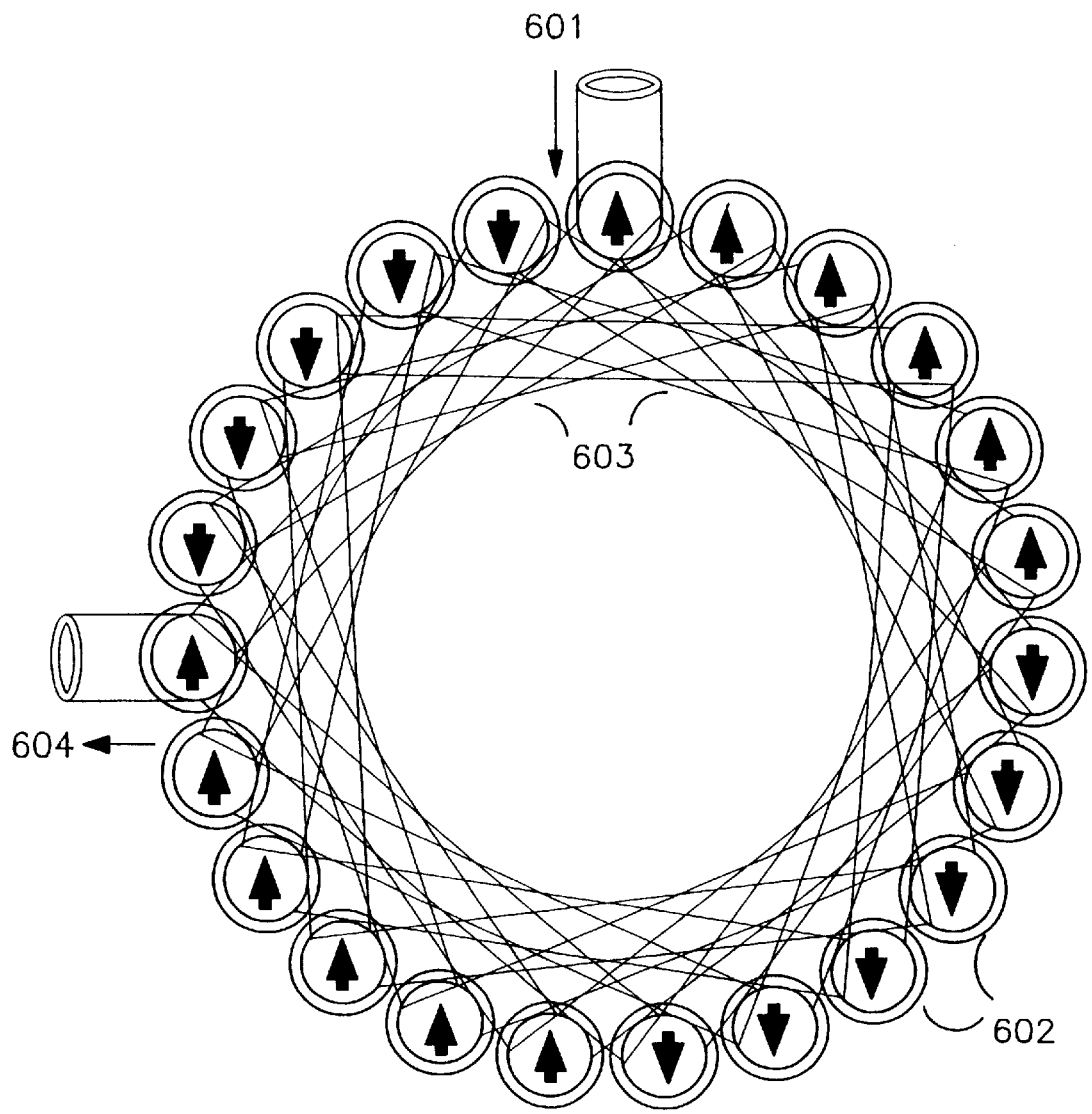

In this embodiment of the invention, fluid flows from the separation system to the disinfection system. A fluid flow rate can be established to prevent occlusion of UV transmissible surfaces and to scour these same surfaces, as well as all surfaces in the tubing system. Fluid is than disinfected by treatment with ultraviolet radiation which may be applied from ultraviolet lamps submerged within or kept separated from fluid. Submerged lamps generally require protection from the fluid such as a quartz jacket or coating that allows for a high transfer of UV radiation while preventing damage to the UV lamps. One example of a design for a tubing system is depicted in FIG. 6A with an example of a cross section of a similar tubing system depicted in FIG. 6B. As shown, inlet 601 allows for entry of the fluid into the tubing system composed of rigid (e.g. quartz) tubing 602. Connector elbows 603 allow the system to be compact providing for maximal exposure of fluid to UV lamps positioned within and around the tubing until the fluid departs from the system through outlet 604. Void spaces between longitudinal sections of tubing can be minimized by optimizing the design of interconnections between sections (FIG. 6B). Preferably, the disinfection system is a dry system where the UV lamps are placed in close proximity to, but not within the fluid. This allows for easy UV lamp replacement and heat generated from the UV lamps can be disseminated without damaging the fluid. A dry system requires infrequent maintenance, a real advantage for this design. In one embodiment of the invention, ultraviolet treatment is applied at greater than about 12,000 microwatt seconds per $cm^2$ of radiation, preferably greater than about 20,000 microwatt seconds per $cm^2$, and more preferably greater than about 40,000 microwatt seconds per $cm^2$. In the absence of a minimum amount of contaminants, as determined by flow speeds, fluid can be successfully exposed to the killing effects of ultraviolet radiation.

The invention possesses many additional advantages. As neither magnetic treatment nor ultraviolet radiation add chemicals to the fluid or modify fluid components, the process has no effect on the functionality of the fluid. A need for chemicals such as germicides and biocides, presently used in the disinfectant of fluids, is greatly reduced or completely eliminated. Examples include bromine, chlorine and tricine. As biocides are themselves expensive and pose serious health risks to workers, the savings can be considerable. In addition, many chemicals are detrimental to the efficiency and integrity of the fluid. Consequently, use of the methods and apparatus of the invention greatly extends the useful life and/or shelf-life of the fluid. In addition, odors from contaminated fluid and some biocides can be fairly unpleasant. Use of the invention also reduces or eliminates such odors providing an improved air quality and working environment.

Using the disinfection processes and apparatus of the invention, bacteria counts acceptable to federal (e.g. EPA or FDA), state or local regulations and various other health fields can be set for a particular fluid. The invention allows for the possibility of multiple passes of the fluids to achieve such set microbial levels. Further, the invention provides a controllable resident time in the UV system of exposure to UV radiation for seconds or minutes. For example, in one test using industrial fluid, a bacteria count before coolant was processed through the oil separator and UV system was approximately $10^3$ to $10^6$ microorganism per ml. After a 24 hour cycle, the microorganisms count was almost zero. With this process, costs for the disposal of contaminated coolants and for coolant replacement are substantially reduced. In addition, chemical pollution to the environment is minimized or can be avoided where processes are available for recycling used fluids. In addition, microbial counts following UV treatment of substantially opaque fluids can be further reduced by introducing turbulence to the fluid flow path thereby bringing bacteria to the fluid surface for greater killing exposure.

The methods and apparatus of the invention can be used in both closed and open systems. In closed systems, such as both large and small scale assembly lines and other manufacturing lines, fluids such as coolants flow down the line to cool and lubricate machine tools. Coolants are heat transfer mediums or thermofors and may be in liquid or a gaseous form having the property of absorbing heat from the environment and transferring that heat effectively away from the source. As such, coolants are used in the transportation industry, the tool manufacture industry and in most every small to large manufacturing plant. Coolants, as do most industrial fluids, come in a variety of colors such as gray, red, yellow, white, green and blue, and may be fairly thick in composition as compared to plain water. Types of coolants include petroleum-based, machine fluids and lubricating oils, oil-soluble cutting fluids, semi-synthetic fluids composed of a combination of soluble oils and synthetic oils, synthetic fluids for cutting and grinding both ferrous and non-ferrous alloys, propylene and ethylene glycol and Dowtherm. In addition, some coolants are anti-freezes such as, for example, propylene glycol.

In the assembly and manufacturing lines, coolants pick up a substantial amount of contaminants. Substantial means that the level of contaminants are increased so as to shorten the normal useful life of the fluid due to their concentration and interference with coolant function and to the presence of an enhanced environment for microbial growth. Particles such as metallic or plastic filings or iron or steel chips, typically accumulate on and in the machines being cooled. Particles such as microorganisms, insects, insect parts and other debris also collect in the reservoir and in the lines. These particles are all swept-up in the fluid flow. Other contaminants include lubricating oils, pretreating oils, hydraulic fluids and way oils. Lubricating oils have a low viscosity, compared to way oils which are quite viscous (i.e. heavy oils and oils with long carbon chains). Tramp oils (i.e. renegade contaminant oils that get into machine operations), which typically include way oils, also accumulate in the fluid. These contaminant substances are sticky, adhere to the walls of pipes and the UV system components, and further encourage microbial growth, especially bacterial growth in the line and in the fluid reservoir. Such substances also bind bacteria to their molecular interface surfaces. Preferably, these bacteria are removed during a physical separation step thereby reducing the requirement of the ultraviolet to be the sole bacterial control mechanism.

In the disinfection process, coolant is subjected to filtration by passing the coolant through a prefilter to remove larger particles and debris. The prefiltered fluid is passed through a first stage filter that removes finer particulate matter. Such filters remove particles of greater than about 100 microns, preferably greater than about 50 microns, more preferably greater than about 25 microns and still more preferably greater than about 10 microns. Other contaminants, such as way and other tramp oils are removed using one or more oil separators which are, preferably, dedicated to the removal of such contaminants. In specific instances it may be desirable to design the system to allow specific contaminants, such as molecular iron and iron-containing complexes, to remain. Such complexes can aid in disinfection, for example, in the formation of ferrates.

Liquid contaminants in a contaminated fluid vary greatly depending on the type of fluid and the use to which the fluid is applied. For example, the principal liquid contaminants in an industrial fluid are heavy oils such as way oils and require an oil separation system for removal to allow recycling of the fluid. Many techniques for the removal of oil from a continuous or running stream of fluid are well-known to those of ordinary skill in the art. For example, at least most of the oil can be removed from a fluid by passing the fluid through a plurality of oil separators. Preferably, one of such oil separators is a coalescent filter. Coalescent filters comprise fibers with predefined pore sizes wherein the fibers are adherent to the contaminants. Such filters are commercially available (U.F. Strainrite, Inc; Lewiston Me.). Other oil separators useful according to the methods of the invention include oil skimmers and density centrifuges. Preferably, the pretreatment steps include a strainer step to remove particles of greater than about 100 microns, a centrifugation step to remove a large portion of the heavy oil contaminants, a prefilter step to remove contaminants of greater than about 25 microns, and a coalescent filter for removal of oil and small contaminants.

Figure 7:
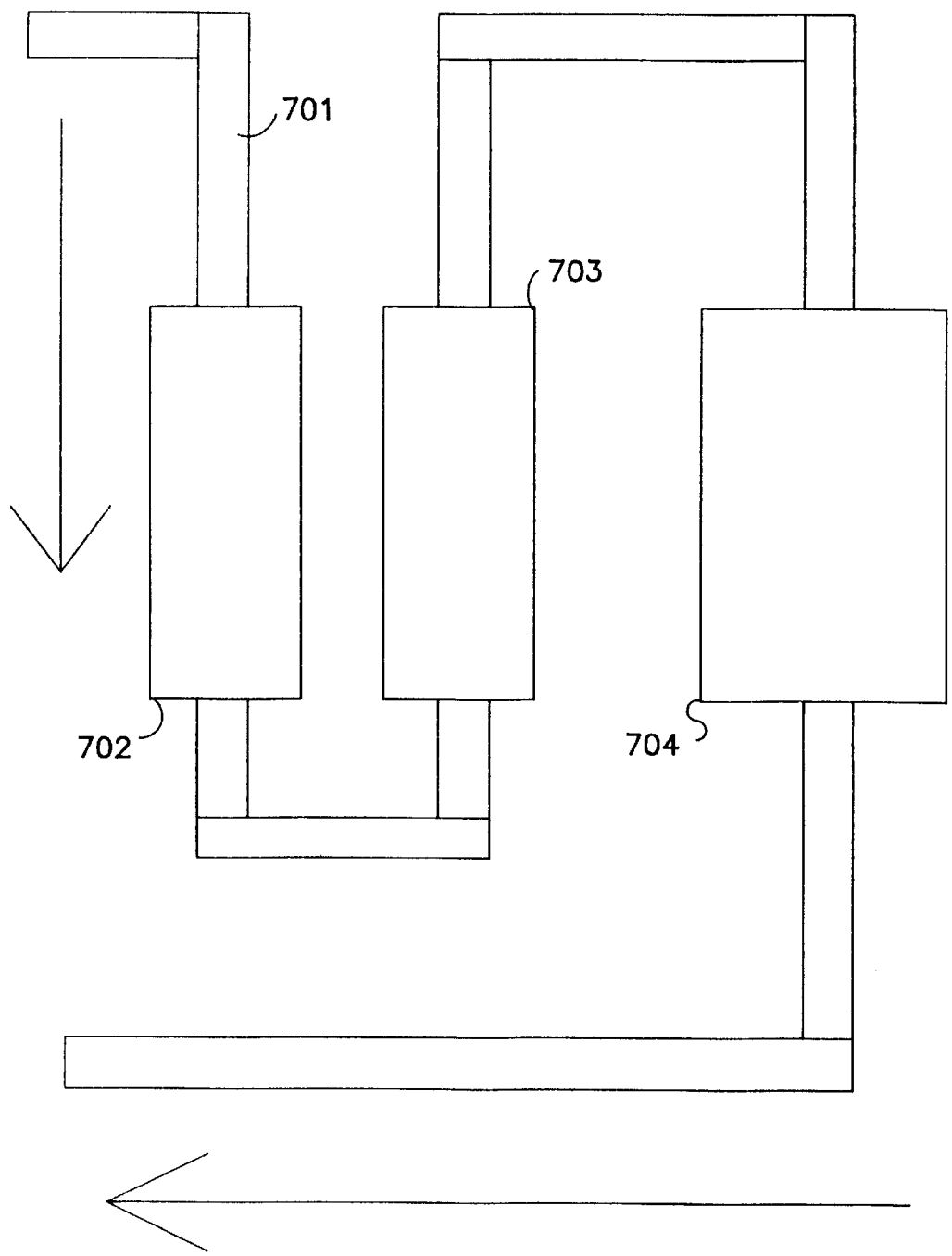
FIG. 7 Oil separation scheme.

An oil separation scheme that is useful for the methods of the invention is depicted in FIG. 7. As shown, fluid flows through tubing system 701 in the directions indicated by the arrows. Fluid first passes through the magnetic field at magnet unit 702 (for oil separation and scale control), downstream to oil separation unit 703, and continues to UV disinfection unit 704. Oil separation unit 703 may contain an oil adsorption material such as, for example, particulate copolymers, polypropylene, polyester, peat, kenaf, cellulose fibers or combinations of these materials, or one or more conventional oil separation devices such as, for example, a cyclonic separator, a filter bag, a coalescent filter, a skimmer or a centrifuge. Each of the devices can be used to remove contaminating oil from the fluid and the oil will be more effectively removed due to the immediately prior magnetic treatment.

Oil adsorbents are highly useful materials and can collect many times their weight in oil and other liquids. Biomass materials such as, for example, peat and kenaf are non-abrasive adsorbents, and are preferred adsorbents for the separation of contaminants. Peat adsorbs polar organic substances and can be used raw, aged or semi-aged with or without mechanical drying. Aged peat is more useful for adsorbing compounds containing carboxyl groups. Semi-aged peat is more useful for adsorbing amine group-containing compounds. Peat and kenaf, another plant material, are also useful for adsorbing heavy metals and most all hydrocarbons. In fact, kenaf adsorbs ten times its ashed weight of oil. Synthetic materials can also be used as adsorbents including polyethylene and polyester. One of the advantages for these materials is that as an adsorbent in a fluid flow, they do not contribute to the carbon loading of the fluid. Further, these materials are extremely user friendly and can be molded into a shape suitable for most any operational condition. Adsorbent can be packaged as sheets or blocks, particularized, powdered or in a mesh, and packaged into bags or retaining vessels. Further, these materials are fairly inexpensive and straightforward to maintain or replace.

Once less than a specified level of contaminants has been reached, the contaminant-reduced fluid can be successfully irradiated with a disinfecting amount of ultraviolet radiation such that any contaminants that remain do not interfere with disinfection of the fluid. The disinfecting amount of radiation depends on the flow rate and volume of the fluid being treated at any one moment. For most applications, radiation is administered at from at least about 15,000 microwatt seconds/cm$^2$ or more, depending also on the type of ultraviolet lamps, the ultraviolet transmissibility of the tubing, the orientation of lamps around the fluid-filled tubes and the structure of the tubing (e.g. flat verses rounded). As the UV lamps can be separated from the fluid, the method is preferably a dry disinfecting system. Although generally not required or necessary, it is also possible to sterilize a fluid by increasing the amount of ultraviolet radiation administered. Ordinarily, though, sterilization is not required to maintain a safe and workable cooling system.

The oil separator and the ultraviolet radiation generating system can be designed as modular units to further increase convenience and to reduce overall costs. As such, the system can be operated continuously, subject to periodic maintenance for UV lamp changes or removal of accumulated contaminants, for a period of greater than one week, greater that one month, greater than one year or even longer.

All types of conventional radiation treatment can be administered to the contaminant-reduced fluid including treatment methods described in U.S. Pat. No. 4,798,702, for use of corrugated ultraviolet-transmissible tubing, U.S. Pat. Nos. 4,971,687 and 4,968,891, for use of thin films, U.S. Pat. No. 5,494,585 for use of a cavitation process, and U.S. Pat. Nos. 3,527,940 and 4,766,312, for maximizing radiation treatment by passing fluids through a helical path. In addition, such radiation can include ionizing radiation, such as gamma radiation or x-rays in place of ultraviolet. Thin films may be shaped by the structure of a portion of the ultraviolet transmissible tube. The fluid may be guided into a thin film with a thickness of less than about 5 mm, preferably less than about 4 mm, and more preferably less than about 2 mm. As radiation of substantially opaque fluids can disinfect about 1 mm to about 1.5 mm of fluid, radiation transmitted from all sides of a 2 mm to 3 mm fluid flow can be disinfected. Where complete sterilization of the fluid is desired, thin film technology may be useful. A wide variety of ultraviolet sterilization devices or self-contained units can be used with one or a plurality of ultraviolet lamps both within, between and surrounding the tubing.

Figure 8:
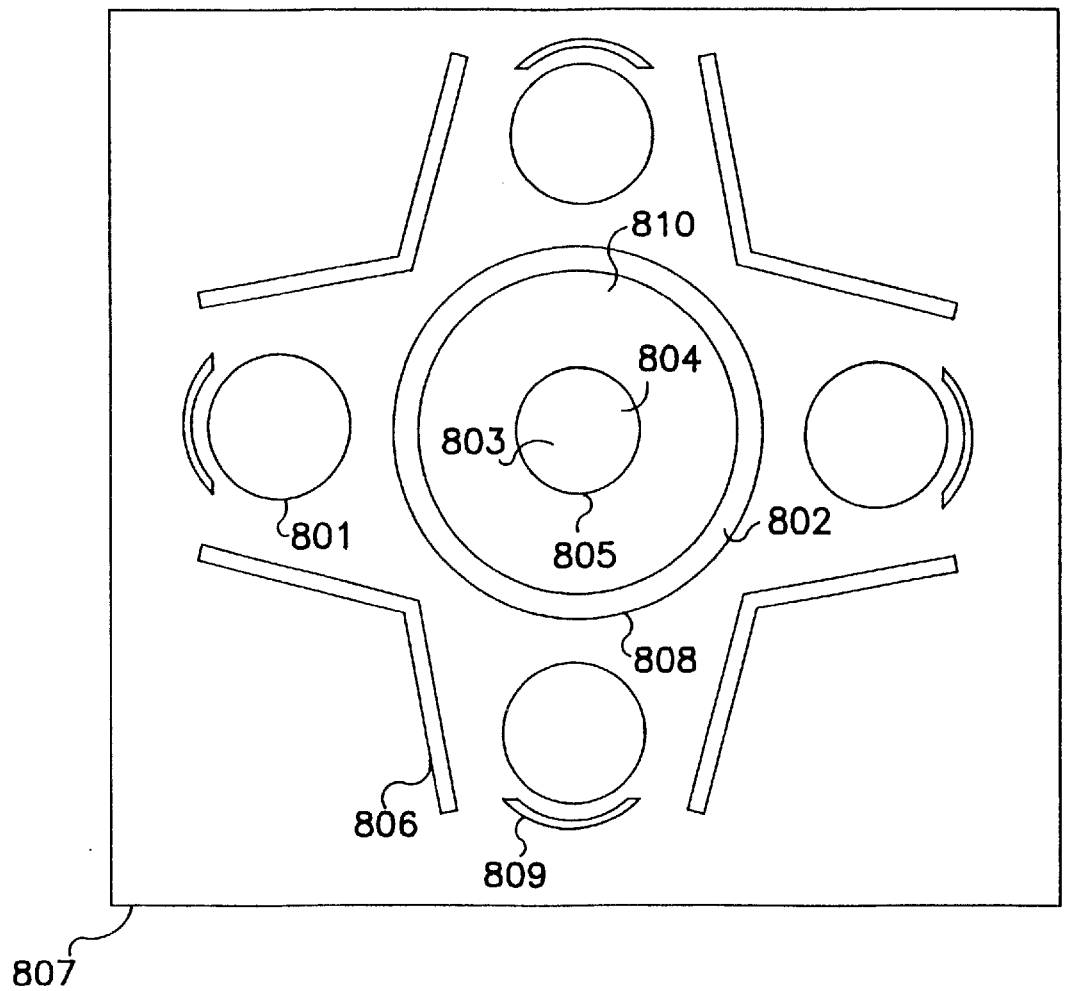
FIG. 8 Cross section of fluid pipe and surrounding UV system.

Tubing and thus fluid exposure to the radiation can be optimized by creating an orientation pattern of UV lamps around the tubing with ultraviolet reflective surfaces directing the radiation toward the fluid. Radiation exposure is highest at the fluid-surface interface. A cross-section of a fluid pipe 802 with a surrounding UV system is shown in FIG. 8. As depicted, ultraviolet lamps 801 radiate energy into a fluid contained within UV-transmissible tube 802. With opaque fluids, this tube may contain a tube within a tube configuration. A hollow tube or solid center 803 is surrounded by wall 804 the surface of which is coated with UV reflective material 805. With opaque fluids, tube 802 may contain inner tube 803 which may be hollow and transmit air under pressure discharged through walls 804 or through pores in walls 804 to create turbulence. UV reflective material is also present on UV reflectors 806 positioned around tube 802 so as to maximize energy input to fluid flow 810. Additionally, reflectors 809 may be placed in close proximity to UV lamps 801 to optimize reflection of UV radiation to UV transmissible tube 802. Alternatively, 803 may be a bead, cone or other mechanism linked by filament as in a chain to create turbulence within passing fluid. Ribs 808 are present on inner surface of wall 804 to generate turbulence within fluid flow 810. Alternatively, fluid flow 807 through tube 802 may be in the form of a thin film to allow for complete penetration of UV radiation. Thin film depth will depend on the opacity or translucency of the fluid and, in general, opaque thin films will have a depth of less than about 3 mm and transparent thin films will have a depth of greater than about 3 mm.

Ultraviolet reflective material includes, for example, an aluminum, a titanium or titanium nitrate based material, or a combination thereof. Preferably, the reflector is coated by a sputtering process whereby the coating material is deposited in a vacuum onto a solid support such as an aluminum or teflon surface. In addition, UV lamps may be partially coated with UV reflector substances or UV blocking substances to reflect and to direct energy output and/or prevent exposure of other surfaces to UV radiation.

Many types of reflectors are known to those of ordinary skill including polished aluminum reflectors, described in U.S. Pat. No. 4,534,282, reflectors mounted to the frame, described in U.S. Pat. No. 3,634,025, elongated curved reflectors, described in U.S. Pat. No. 4,766,321 and outward reflecting reflectors.

As known to those of ordinary skill in the art, ultraviolet radiation can be directed to kill eukaryotic cells, bacterial cells, fungi and spores, virus particles and almost any living microorganism. Based on the intensity of the radiation treatment, one of ordinary skill can choose to disinfect or completely sterilize the fluid. Sterilization is usually unnecessary for industrial fluids, but is often required to meet EPA or FDA guidelines for products regulated by government guidelines such as pharmaceuticals and animal products.

Industrial fluids, for example, typically contain between about $10^5$ to about $10^9$ bacteria per ml. Reduction of bacterial levels to at or less than about $10^3$ is generally required to provide a safe and risk-free working environment as well as to extend coolant life. Treatment of contaminated fluid, according to the methods of the invention, kills greater than 90% of the microorganisms in the contaminated fluid, preferably greater than 95%, and more preferably greater than 99%. This reduces the bacterial load of the fluid by at least about one log, preferably at least about 2 logs, more preferably at least about 3 logs. Increased disinfection is possible by incorporating multiple exposure passes to decrease the bacterial load of the fluid at least about 4 logs, preferably at least about 5 logs, and more preferably at least about 6 logs or more when necessary. Alternatively, it may only be necessary to remove or kill less than 10% of the microbial contaminants provided the system is operated continuously with the fluid repeatedly passed through the disinfection system. In this manner, a continual reduction of 10% per pass or per total turnover of the fluid volume will reduce microbial contamination to near zero in a set time frame. Treatment times and rates vary depending on the volume of fluid being treated and the amount of contamination, the rate of fluid flow and the rate of surviving microorganism growth that would depend on the level of biocide in the system and the nature of the other components within the fluid. Therefore, treatment may be performed, for example, in a continuous system operated for months, weeks, days or hours to reduce the bacterial load to desired levels and to maintain such levels.

Disinfection methods may be further enhanced by establishing turbulence generating systems in the fluid stream during irradiation. As ultraviolet radiation cannot pass more than about 1 mm to about 2 mm into most fluids, and less than 1 mm in opaque fluids, it is important to maximize exposure of the microorganisms in the fluid to ultraviolet radiation. As fluid travels transversely as in a turbulent or non-laminar manner to fluid flow in the tubing, there is a greater likelihood that the microorganisms in the fluid will be subjected to ultraviolet treatment. Turbulence should be sufficient to provide a Reynolds number greater than that defining a laminar flow or greater than about 4,000 and preferably greater than about 10,000. By encouraging microorganisms to move transversely, microbes are brought to the surface of the fluid at the inner surface of the UV-transmissible tubing and not hidden within mid-sections of the tube. Passage of fluid and microorganisms within the fluid are moved from zones of no or low UV radiation to surface zones of high UV radiation. In this manner not only is killing effect magnified, but the turbulence creates a scouring effect within the tubing. Radiation can also induce oxidation of certain chemicals that may be present in the fluid which may add to both the scouring and killing effects.

Tube sizes that guide the flow of turbulent fluid are not limited by the ability of UV radiation to penetrate the fluid. Tube diameters which can be utilized for this method may have a diameter of greater than about 4 mm, preferably greater than about 6 mm, and more preferably greater than about 10 mm or more. Tube sizes of greater than two inches, greater than three inches and even greater than four inches, typical in most industrial settings where the fluid is more translucent and less opaque, are also applicable to this method.

Turbulence-generating systems that encourage transverse motion include aeration systems that create gaseous bubbles within the tube. Preferably, the gas does not interact with the fluid components. Typical gasses that can be used for most fluids include, for example, air, carbon dioxide, oxygen, hydrogen, helium, nitrogen, argon and combinations of gasses, any of which may be pressurized. In addition, this technique is not limited to gas. Liquids may be forced into the inner tube as well creating turbulence in the fluid as the liquid exits holes within the inner tubing walls. Liquids which can be used include the liquid itself, which may be the contaminated liquid or liquid that has been treated according to the invention, an inert liquid or another liquid that does not negatively interact with the fluid being treated. The tube within a tube configuration preferably has a controllable pressure differential within the tubing.

Turbulence can also be generated by suspending articles within the fluid stream such as, for example, ridges, helical vanes, impellers, baffles, projections, vanes, paddles, wheels, beads, cones or slotted cones, or almost any geometric structure. Such structures or turbulators or agitators may be on a string, free in the fluid or free, but confined in a section of the tubing. Such structures may be constructed of a metal such as steel or a composite polymer. The beaded string is placed into the lumen of a tube along the direction of fluid flow. As fluid impacts the bead, fluid is directed transversely or turbulently to the sides of the tube where ultraviolet radiation exposure is maximized. Preferably, the bead is slightly smaller than the lumen of the tube. However, a variety of sizes may be utilized the only requirement being that they fit within the lumen and not cause an impractical or high head pressure in the system. Such devices have the further advantage that they can be easily replaced without requiring replacement of the entire tubing system. Combinations of these techniques may also be utilized.

Another embodiment of the invention is directed to combinations of fluid disinfection treatments such as those described above. Fluids may be treated with a combination of contaminant removal and turbulence generation followed by radiation treatments. Such treatments may be further supplemented with conventional treatments such as, for example, filtration, centrifugation and the addition of biocides including anti-bacterial and anti-fungal agents. However, as the combination is highly effective, the amount of biocidal agents that are added can be greatly reduced as compared to conventional methods. The working environment would be improved due, in part, to the lack of noxious fumes caused by microbe-induced decaying fluid, and the lack of biocides and/or microorganisms, greatly improving air quality. Health risks to workers are also greatly reduced.

Another embodiment of the invention is directed to an apparatus for disinfecting a fluid. The apparatus comprises a tubing system, a magnet, which may be a permanent magnet or electromagnet, an ultraviolet radiation-treatment system, a turbulence-generating system and/or a contaminant-separation system which, for example, may be specific for particles, microbes, oil or a combination of these contaminants.

In a dry modular apparatus, the tubing system guides the passage of the fluid at a determinable flow rate through the apparatus with the UV lamps separated from the fluid. Tubing of the system is composed of ultraviolet-transmissible material such as, for example, a fluoropolymer, as described in U.S. Pat. No. 4,798,702. Tubing which is useful for the tubing system should preferably be capable of withstanding pressures of greater than about 70 psi, and preferably greater than 150 psi, have a thickness of between about 20 to about 80, and more preferably 60, thousandths of an inch, and be transmissible to greater than 40% of the ultraviolet radiation being applied, preferably greater than 50% and more preferably greater than 60%. A preferred type of tubing has been identified and is composed of monofluoroalkyoxy polymer, perfluoroalkoxy polymer (Zeus Industrial Products, Inc.; Orangeburg, S.C.), Hyflon MFA which is a co-polymerization of tetrafluoroethylene and perfluoromethylvinyl ether, or fluorinated ethylene propylene (FEP) (Product No. 3E 750 SW 0; Zeus Industrial Products, Inc.; Orangeburg, S.C.). These types of tubing are resistant to fouling, have a high corrosion resistance, are both strong and light weight, and are highly UV transmissible with transmission factors of greater than about 55%. Preferably, the tubing is flattened or oval shaped with a cross-sectional diameter ratio of about 1 to about 0.35. Surface area exposed to UV radiation is increased and the surface area of tubing shadowed by adjacent coils of the same spiral or by the coiled lengths of tubing are minimized. The flatted surface may be modified to increase the wetted surface area by incorporation of longitudinal serrations, coarse serrations or waves. These modifications increase UV effectiveness by increasing the area of the fluid exposed to the UV radiation.

The tubing system may also comprise one or more inlet and outlet ports attached to opposite ends of a coiled tube. The inlet ports allow for the flow of fluid from the line or the reservoir into the disinfection unit. The outlet port allows for the flow of disinfected fluid back to the line such as a manufacturing or assembly line. Tube surfaces may be smooth, furrowed, wrinkled, indented, transverse ridged or corrugated, and the tubing may be coiled, parallel, twisted, conical, serpentine or in a helix at the point of radiation treatment. Ultraviolet lamps can be positioned outside and inside the tubing configuration as well as between the tubes. Tubing has a flattened to rounded cross section (e.g. oval). However, the system may be configured to create a thin film of fluid (flattened) at the point of radiation treatment to maximize radiation exposure.

The contaminant separation system can be designed to remove particulate and other contaminants from the fluid. Particulate matter can be removed with filters having pore sizes designed to remove particles of greater than 100 micron, preferably greater than 50 micron, and more preferably greater than about 10 micron. The contaminant separation system may contain an oil separator designed to remove at least most of the oil from the fluid. Examples of suitable types of oil separators include skimmers, centrifuges and coalescent separators. Other unwanted liquids can be removed by a separation means particular to the type of liquid. Such separation means are known to those of ordinary skill in the art.

In addition to a contaminant separation system, the apparatus may also includes an ultraviolet radiation system. The radiation system is comprised of one or more ultraviolet lamps in close proximity to the tubing system. As the lamps do not come into direct contact with the fluid, the apparatus may be described as a dry system (i.e. the lamp does not come into direct contact with the fluid contained within the UV-transmissible tube). In a dry system, fluid components are not subjected to unwanted heating from the UV lamps. Further, the UV lamps are not cooled by circulating fluid and, therefore, maintain a temperature high enough for optimum generation of UV radiation. Also, maintenance of lamps is minimized due to the separation of dirty or contaminated fluid from the lamp surfaces. Preferably, there are a plurality of ultraviolet lamps surrounding a coiled tube on both the inside and outside, and even between, the coils. As the energy imparted to the target fluid is proportional to the square of the distance of the UV lamps to the fluid, that distance should be minimized to maximize the amount of energy transmitted to the fluid. The unit can be ventilated or air conditioned to prevent heat build-up as necessary to prolong the life of the UV lamps and so as not to damage the fluid.

The apparatus may also comprise tanks or other fluid retention vessels that are temperature regulated. Cooling or heating of the fluid is sometimes necessary for transportation such as, for example, in the transportation of beverages (e.g. soft drinks, beer, wine). Further, the apparatus may also comprise a microorganism detection system. This system would screen for harmful microorganisms in the fluid such as infectious bacteria (e.g. Salmonella, E. Coli, V. cholerae, Shigella), virus (e.g. Hepatitis, poliovirus) or fungi (e.g. Cryptococcus, Candida, Paracoccidioides) in a water supply to be made potable. Multiple detection devices and methods are known to those of ordinary skill in the art and can be coupled electronically for the automatic addition of biocides or the control of UV radiation treatment times or intensities. Such devices may be immunologically-based methods of detection with results measured by optical (e.g. colorimetric), luminescent (e.g. luciferin) or enzymatic (e.g. alkaline phosphatase) means.

Figure 10:
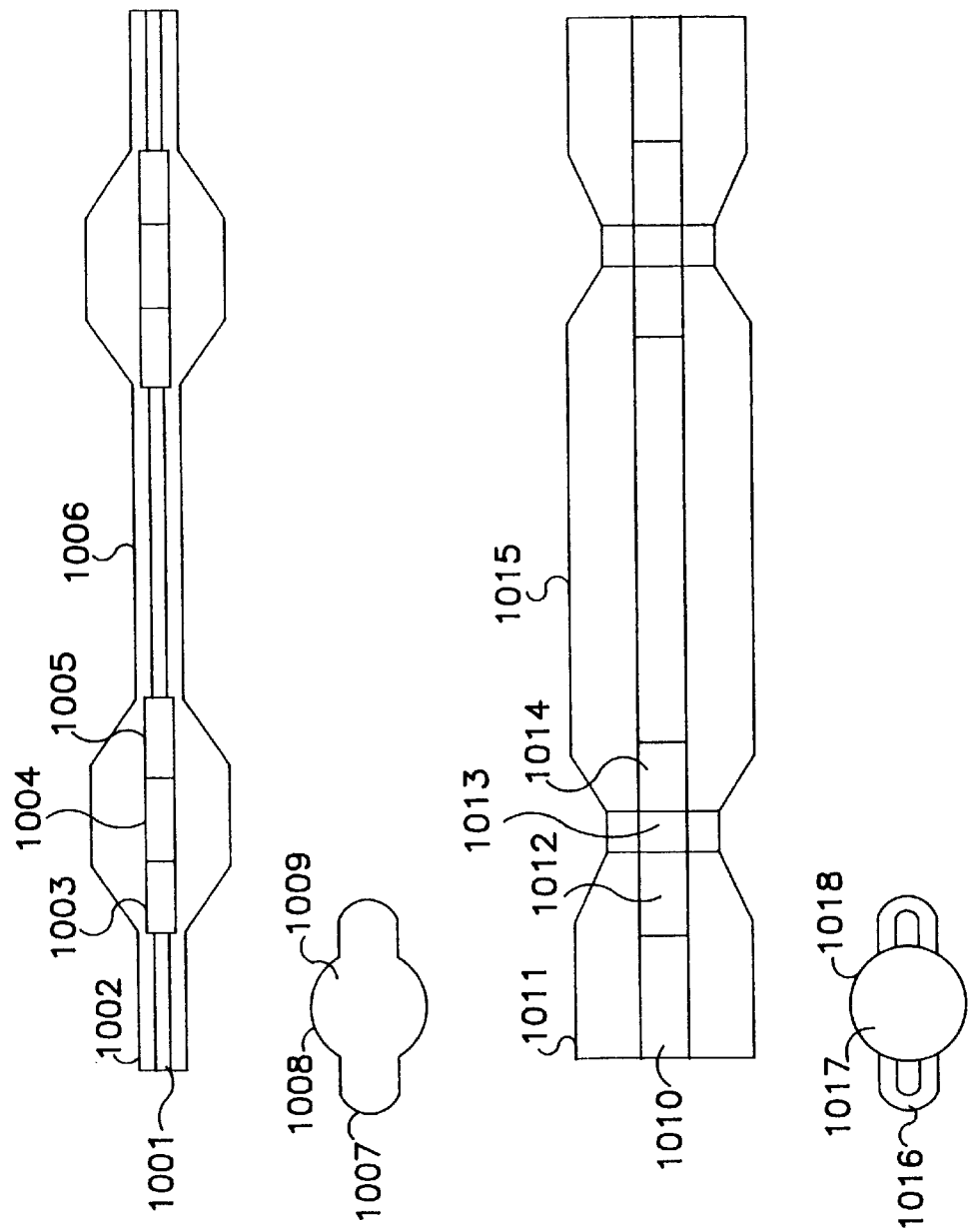
FIG. 10 Tubing structure in both longitudinal and cross-section showing periodic shape modifications for generating turbulence.

The apparatus may also contain a turbulence-generating system to maximize exposure of the fluid to the radiation. The turbulence-generating system should preferably be placed into the tubing wherein the fluid is exposed to the radiation. Examples of turbulence-generating systems include structures attached to the walls of the tube or otherwise free-floating in specified areas of the lumen of the tube. Such structures include nearly any shaped article such as paddles, beads, cones, vanes, ribbons and the like, any of which may be slotted, and which may be fixed to tubing walls, attached to each other or attached to a string and suspended in the fluid. Fixed structures may be placed at set angles to the laminar flow of the fluid, preferably up to about 90°, such as, for example, about 20°, about 30°, about 45°, about 60° or about 75°. Other turbulence-generating systems include tube within a tube configurations that allow for a pressure differential, ultrasonic vibrations, split-flow systems or aeration within the fluid. Another turbulence generating mechanism, which does not require intrusion into the lumen of the tube, comprises a periodic modification of tubing cross sectional shape. For example, rounded tubing may be flattened at regularly or irregularly spaced intervals. As shown in FIG. 10, fluid enters the tubing system through fluid entry port 1001 of flattened tubing 1002 traveling through transition zone 1003 to circular zone 1004 and to another transition zone 1005 and returning to flattened tubing 1006. In cross section, flattened tubing 1007 extends longitudinally from circular zone 1008 containing lumen 1009. Alternatively, flattened tubing may be rounded at spaced intervals. As also shown in FIG. 10, fluid enters the tubing system through fluid entry port 1010 of rounded tubing 1011 traveling through transition zone 1012 to flattened zone 1013 and to another transition zone 1014 and returning to rounded tubing 1015. In cross section, rounded tubing 1017 extends circularly from flattened zone 1016 containing lumen 1018. The apparatus may also contain circuitry appropriate for proper monitoring and control of all aspects of the apparatus. The additional of computer control can also be utilized to create units that are completely or partially automated.

Another feature of the invention is that disinfection units, comprising an apparatus for performing a method of the invention, can be completely portable. Units do not require bulky machinery, or attachment to fixed structures. Portable apparatus can be transported by land, sea or air, and set up in most any location. Power supplies required to operate the unit are not onerous and can also be provided from portable sources including solar or wind power. As such, apparatus of the invention can be used in remote locations for temporary or permanent water purification by civilians or military personnel. No specialized training is required to operate a unit other than basic information. Further, as the apparatus can be self-contained, no on-site construction is required. The unit can be transported intact to the desired location.

Another embodiment of the invention is directed to fluids treated according to the methods of the invention. Such fluids include liquid which, after treatment, are substantially free of microbial contamination and, optionally, other contaminants as well as way and tramp oils, microbial particles and other particulate materials. Substantially free means that the population level of microbes has been reduced to a level that does not pose a risk to workers, resulting in an improved quality to the working environment. Such fluids include machine tool coolants, machine tool lubricants, electrodischarge machine fluid, Zyglo, electro-coating fluid, chassis-washing fluid, top-coating fluids, sonic-bath fluids, spot- and steam-welding coolants, electron-beam and laser-welding coolants, test-cell waters for metal processing, plastic molding and forming coolants, quenching fluids, recycled and recirculation fluids and combinations thereof.

Additional fluids include petroleum products and petrochemicals such as, for example, petrolatum, natural gas, gasoline including diesel fuel, kerosene and all forms of fuel for internal combustion engines, ethylene, ammonia, synthetic petrochemicals, fertilizers, paraffin, naphthene, alcohols such as methanol ethanol and butanol, paints, solvents and other like chemical compounds. Yet other fluids including water such as potable water, water to be consumed in areas of suspected contamination, water supplies from natural or man-made emergencies, water used during military operations, third-world water supplies, livestock water and beverages such as, for example, flavored and plain water, flavored drinks and drink blends, vegetable, fruit and other juices, soft drinks, beer, wine and other liquors, may also be treated according to the method of the invention.

The following examples illustrate embodiments of the invention, but should not be viewed as limiting the scope of the invention.

EXAMPLES

Example 1
A Magnetic/UV Disinfection Apparatus.

Figure 9:
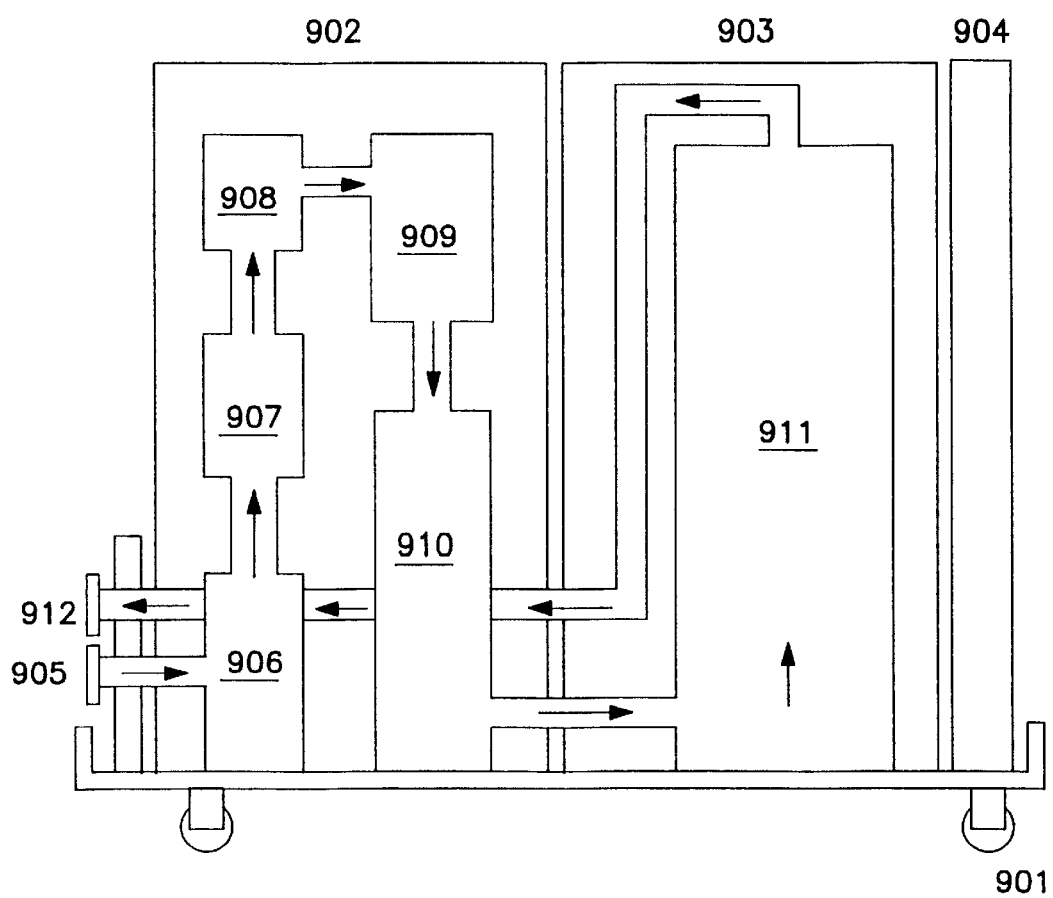
FIG. 9 A model filtration/germicidal system.

An example of one embodiment of the invention, an apparatus, is shown in FIG. 9. As shown, the apparatus is entirely contained on mobile cart 901 which is on casters and, consequently, quite mobile. The basic unit comprises preparation 902, ultraviolet module 903 and electronics module 904, which may contain a fan for internal temperature regulation, gauges reporting on the condition of the unit and/or the status of the fluid flow, indicator lamps and control switches. Fluid enters through inlet port 905, is forced by pump 906 thorough the apparatus to first magnet 907 for enhanced oil removal, to second magnet 908 for removal of ferrous and ferric complexes that could foul the UV transmissible tubing, block UV radiation and corroding metallic materials in the system, and to prefilter 909. From prefilter 909 fluid travels through main filter 910 where the largest portion of contaminating materials are removed. Filtered fluid is passed to UV unit 911 where the fluid is disinfected and the disinfected fluid is expelled through outlet port 912. As the unit is dry modular in design, it can be used to disinfect many different types of fluids.

According to an embodiment of the general process of the invention, coolant to be disinfected is first treated by passing through a screen to remove metallic particles and other debris. Coolant is next run through an on site commercial centrifuge to reduce contaminant concentrations to approximately two percent. Coolant to be treated is drawn into the system by a pump mechanism. The pump forces coolant into a first magnet to remove ferrous and ferric complexes. The fluid than passes to a second magnet that modifies contaminants so as to increase hydrophobicity and molecular shape. The fluid is then forced into an oil separator device containing a filter vessel under pressure which contains a filter cartridge. The cartridge will normally contain a 10 to 20 micrometer pore size which facilitates separation of the oil and binding of the oil to the fiber structure of the cartridge. Such filtration performs the important role of removing large amounts of both living and dead bacteria. Removal of the dead bacteria reduces nutrient loading in the fluid. The differential pressure between the input and the output of the filter vessel is used to monitor the condition of the filter cartridge and can be read at the electronic module. When the pressure reaches the specified differential, in most cases the greatest differential, the filter cartridge has filled with contaminant oil and must be replaced. Rate of oil accumulation will vary depending upon the amount of oil in the coolant and the viscosity of the oil as well as the type of coolant. The fluid is forced under pressure into the germicidal module and disinfected before being discharged from the outlet.

Example 2
System Designs for Selected Fluids.

System designs for selected fluids, shown in Table 1, are designed to provide a useful combination of treatments and exposures for individual types of fluids.

TABLE 1

Selected System Designs

| SYSTEM | SEQUENCE | FLUIDS |
| --- | --- | --- |
| No. 1 | UV | Water, clean fluids; clear or opaque fluids |
| No. 2 | Screen-Oil Separator Filter | Industrial fluids such as chassis wash fluids, electrocoat fluids and topcoating |
| No. 3 | Screen-Oil Separator Filter-UV | As in No. 2 adding contaminated fluids such as metal working fluids and latex solutions |
| No. 4 | Screen-Pre-filter-Filter separator-UV | Metal cutting fluids, industrial fluids |
| No. 5 | Screen-High gauss magnet-Pre-filter-Oil Separator-UV | Metal cutting fluids, industrial fluids |
| No. 6 | Screen-High gauss magnet-UV | Fuels, e.g. diesel, kerosene |
| No. 7 | Screen-Low velocity First stage magnet-High gauss magnet-Pre-filter-Oil Separator-UV | Metal cutting fluids, industrial fluids |
| No. 8 | Screen-Fe(OH)$_{3-6}$-High gauss magnet-UV | Swimming pool and spa water; industrial fluids not subject to oxidation damage. |
| No. 9 | Screen-Fe(OH)$_{3-6}$-Air-UV-High gauss magnet-UV | Potable water; water to be disinfected for consumption; High potential to kill spores, cysts and parasitic eggs |

TABLE 1-continued

Selected System Designs

| SYSTEM | SEQUENCE | FLUIDS |
| --- | --- | --- |
| No. 10 | Screen-Low velocity First stage magnet-High gauss magnet-Pre-filter-Filter separator-Air-UV | Swimming pool and spa water; industrial fluids not subject to oxidation damage |
| No. 11 | Screen-High gauss magnet | Biocide treated industrial fluids such as metal cutting fluids |
| No. 12 | $Fe(OH)_{3-6}$-UV-High gauss magnet | Biocide treated industrial fluids such as metal cutting fluids |

System 1: Occlusion dependent upon velocity of fluid being treated

System 2: Screen to remove debris in fluid; Hydrocarbon contaminant separation dependent upon pore size and composition of the filter, e.g., coalescer; Fluid velocity of factor. Filter can be composed of standard materials such as polypropylene or nylon or can be composed of peat or kenaf, a southern plant providing increased adsorption capacity and affinity.

System 3: Screen to remove debris in fluid; Hydrocarbon contaminant separation dependent upon pore size and composition of the filter, e.g., coalescer; Fluid velocity of factor. Filter can be composed of standard materials such as polypropylene or nylon or can be composed of peat or kenaf, a southern plant providing increased adsorption capacity and affinity.

System 4: Pre-filter bag removes iron-sludge and particles that would occlude separator filter. Fluid velocity a factor. Other effects as in No. 3.

System 5: Molecule alteration resulting in increased trapping of contaminants given equal size pores as without magnet; Increased filter effect due in part to enhanced polarity of $H_2O$ caused by the magnet. Decreased adherence to fluoropolymer UV tube due to alteration of hydrocarbon side chains. High gauss permanent or electrostatic magnet is one of few forces that can pass directly through solids. This enables creation of flux density that can cause activation of spores, ova, cysts and eggs thereby increasing their susceptibility to other stresses such as, for example, UV or biocides. Magnet also activates metabolism of vegetative cells increasing their susceptibility to other stresses as well. Potential synergism between magnet and UV in affecting target DNA and RNA molecules. Magnetic activation of calcium carbonate, $Fe(OH)_3$, $BaSO_4$, $BaCO_3$, $CaSO_4$ to prevent scaling. Aids flow as well as preventing microbial growth habitat. Other effects as in No. 4.

System 6: Effects as above in No. 4 without filters for fluids that do not contain contaminant hydrocarbon oils.

System 7: Trapping of ferric complexes to reduce fouling of fluoropolymer tubing; reduction of iron-related corrosion. Others effects as in No. 5.

System 8: $Fe(OH)_{3-6}$ introduced to provide disinfecting ferrates which will augment the UV and increased killing potential.

System 9: Introduction of ferrates followed by air and UV will create additional oxidation power of ozone and hydrogen peroxide, especially at low wavelength UV such as 181 nm. Iron catalyzed oxidation of organics. Magnet and final standard UV (253.7 nm) provide synergistic killing power. Others effects as in No. 5.

System 10: Ozone and hydrogen peroxide created—ferric complexes removed; Synergistic killing activity; Magnet effects as in No. 5. Filter system to remove contaminants to prevent occlusion of UV system.

System 11: Magnet serves to enhance dispersion of the biocide within the fluid increasing its effectiveness; Magnet causes activation of spores thereby increasing their susceptibility to biocide.

System 12: Ferrates created to enhance disinfection of biocides; Magnet serves to enhance dispersion of the biocide within the fluid increasing its effectiveness; Magnet causes activation of spores thereby increasing their susceptibility to biocide.

Other embodiments and uses of the invention will be apparent to those skilled in the art from consideration of the specification and practice of the invention disclosed herein. All U.S. patents and other documents referenced herein, for whatever reason, are specifically incorporated by reference. It is intended that the specification and examples be considered exemplary only, with the true scope and spirit of the invention being indicated by the following claims.

We claim:

1. A method for disinfecting a contaminated fluid that is substantially opaque comprising
    passing the fluid through a magnetic field at a velocity of greater than about 1 meter per second and
    irradiating the fluid with a disinfecting amount of ultraviolet radiation without shaping said fluid into a thin film of less than 5 mm.

2. The method of claim 1 wherein the contaminated fluid is an aqueous fluid, an industrial fluid, a combustible fuel or a liquid beverage.

3. The method of claim 1 wherein the contaminated fluid is selected from the group consisting of water to be made potable, beverages, industrial water, coolant, lubricating oil, fuel, petrochemicals, alcohols, acids and combinations thereof.

4. The method of claim 1 wherein the contaminated fluid is an aqueous fluid and said aqueous fluid is passed through the magnetic field at a velocity of from about 2 to about 5 feet per second.

5. The method of claim 1 wherein the contaminated fluid is an organic fluid and said organic fluid is passed through the magnetic field at a velocity of from about 10 to about 50 feet per second.

6. The method of claim 1 wherein the magnetic field is generated by an electromagnet or a permanent magnet.

7. The method of claim 1 wherein the magnetic field strength is between about 600 to about 9,000 gauss.

8. The method of claim 1 further comprising the step of passing said fluid through a contaminant separation system.

9. The method of claim 8 wherein the contaminant separation system comprises one or more filters or oil separators.

10. The method of claim 9 wherein the one or more filters comprises a magnetic filter that removes ferrous and ferric complexes.

11. The method of claim 9 wherein the one or more oil separators contains an oil adsorption material selected from the group consisting of a particulate copolymer, polypropylene, polyester, peat, kenaf, cellulose fibers and combinations thereof.

12. The method of claim 9 wherein the one or more oil separators comprises a cyclonic separator, a filter bag, a coalescent filter, a skimmer, a centrifuge or a combination thereof.

13. The method of claim 1 wherein the contaminated fluid has a bacterial load that is reduced at least 1 log after irradiation.

14. The method of claim 1 wherein the contaminated fluid has a bacterial load that is reduced at least 2 logs after irradiation.

15. The method of claim 1 wherein the contaminated fluid is contained within a closed system and the bacterial load within said system remains below about $10^3$ microorganisms per ml.

16. The method of claim 1 wherein the step of passing said fluid through the electric field reduces scale adherence.

17. The method of claim 1 further comprising the step of creating turbulence in the contaminated fluid during irradiation.

18. The method of claim 17 wherein turbulence is created by shape modification of a tubing system that contains and guides passage of said fluid.

19. A fluid disinfected by the method of claim 1.

20. A method for disinfecting a fluid that is substantially opaque comprising passing oxygenated fluid containing molecular iron through a magnetic field at a velocity of greater than about 1 meter per second wherein said magnetic field is sufficient to form a disinfecting amount of ferrates.

21. The method of claim 20 wherein the fluid is supplemented with an oxidizing agent to form said oxygenated fluid.

22. The method of claim 21 wherein the oxidizing agent is hydrogen peroxide, ozone or a combination thereof.

23. The method of claim 21 wherein the fluid is supplemented with air or oxygen and subsequently treated with sufficient ultraviolet radiation to form said oxidizing agent.

24. The method of claim 20 wherein the disinfecting amount of ferrates is greater than about $10^{-3}$ mM.

25. A fluid disinfected according to the method of claim 20.

26. A method for treating a fluid that is substantially opaque comprised of passing the fluid through a magnetic field and an ultraviolet disinfection system, without shaping said fluid into a thin film of less than 5 mm, at a velocity of greater than about 1 meter per second.

27. The method of claim 26 wherein the fluid is an aqueous fluid, an organic fluid, an industrial fluid or a combustible fluid.

28. The method of claim 27 wherein the combustible fluid is selected from the group consisting of diesel fuel, gasoline, hydraulic fluid, machine oil, natural gas, petrochemicals, alcohols, acids and combinations thereof.

29. The method of claim 26 wherein the magnetic field is generated by an electromagnet or a permanent magnet.

30. The method of claim 26 wherein the magnetic field strength is between about 600 to about 9,000 gauss.

31. The method of claim 26 wherein the fluid disinfection system comprises a microbe filter, ultraviolet or ionizing radiation treatment, ultrasound treatment, heat treatment, the addition of a biocide or pasteurization of said fluid.

32. The method of claim 26 further comprising the step of passing said fluid through one or more filters.

33. The method of claim 32 wherein the one or more filters comprise oil separators, particle filters, or filters containing magnets.

34. A fluid treated by the method of claim 26.

35. A method for disinfecting a contaminated ultraviolet opaque fluid comprising passing the contaminated fluid through a magnetic field and heating the contaminated fluid to a pasteurizing or sterilizing temperature for a period of time.

36. The method of claim 35 wherein the contaminated fluid is an aqueous fluid, an organic fluid, an industrial fluid or a combustible fluid.

37. The method of claim 35 further comprising the step of passing said fluid through one or more filters.

38. A fluid disinfected by the method of claim 35.

* * * * *